(12) United States Patent
Bi et al.

(10) Patent No.: US 12,209,111 B2
(45) Date of Patent: Jan. 28, 2025

(54) TARGETING P18 FOR mTOR-RELATED DISORDERS

(71) Applicant: WESTERN UNIVERSITY OF HEALTH SCIENCES, Pomona, CA (US)

(72) Inventors: Xiaoning Bi, Corona, CA (US); Michel Baudry, Corona, CA (US); Jiandong Sun, Chino Hills, CA (US)

(73) Assignee: WESTERN UNIVERSITY OF HEALTH SCIENCES, Pomona, CA (US)

( * ) Notice: Subject to any disclaimer, the term of this patent is extended or adjusted under 35 U.S.C. 154(b) by 1094 days.

(21) Appl. No.: 17/059,882

(22) PCT Filed: May 31, 2019

(86) PCT No.: PCT/US2019/034898
§ 371 (c)(1),
(2) Date: Nov. 30, 2020

(87) PCT Pub. No.: WO2019/232368
PCT Pub. Date: Dec. 5, 2019

(65) Prior Publication Data
US 2021/0163555 A1 Jun. 3, 2021

Related U.S. Application Data

(60) Provisional application No. 62/678,605, filed on May 31, 2018, provisional application No. 62/678,622, filed on May 31, 2018.

(51) Int. Cl.
| | |
|---|---|
| *C12N 15/113* | (2010.01) |
| *A61P 25/00* | (2006.01) |
| *C07K 14/47* | (2006.01) |
| *A61K 38/00* | (2006.01) |

(52) U.S. Cl.
CPC .......... *C07K 14/4703* (2013.01); *A61P 25/00* (2018.01); *C12N 15/113* (2013.01); *A61K 38/00* (2013.01); *C07K 2319/10* (2013.01); *C12N 2310/122* (2013.01); *C12N 2310/14* (2013.01); *C12N 2310/20* (2017.05)

(58) Field of Classification Search
None
See application file for complete search history.

(56) References Cited

PUBLICATIONS

Li et al., Molecular and Cellular Proteomics, 2017, 16.4:594-607. (Year: 2017).*
Moore et al., Methods Mol Biol. 2010, 619:141-158, author manuscript is 15 pages. (Year: 2010).*

* cited by examiner

*Primary Examiner* — Stacy B Chen
(74) *Attorney, Agent, or Firm* — RAPHAEL BELLUM PLLC

(57) ABSTRACT

Accumulating evidence indicates that the lysosomal Ragulator complex is essential for full activation of the mechanistic target of rapamycin complex 1 (mTORC1). Abnormal mTORC1 activation has been implicated in several developmental neurological disorders, including Angelman syndrome (AS), which is caused by maternal deficiency of the ubiquitin E3 ligase UBE3A. Here, it is reported that Ube3a regulates mTORC1 signaling by targeting p18, a subunit of the Ragulator. Ube3a ubiquinates p18, resulting in its proteasomal degradation, and Ube3a deficiency in the hippocampus of AS mice induces increased lysosomal localization of p18 and other members of the Ragulator-Rag complex, and increased mTORC1 activity. p18 knockdown in hippocampal CA1 neurons of AS mice reduces elevated mTORC1 activity and improves dendritic spine maturation, long-term potentiation (LTP), as well as learning performance. The results described herein indicate that Ube3a-mediated regulation of p18 and subsequent mTORC1 signaling is critical for typical synaptic plasticity, dendritic spine development, and learning and memory.

7 Claims, 17 Drawing Sheets

Specification includes a Sequence Listing.

TARGETING P18 FOR mTOR-RELATED DISORDERS

CROSS-REFERENCE TO RELATED APPLICATIONS

This application claims priority to U.S. Application No. 62/678,605, filed on May 31, 2018, which is incorporated herein by reference in its entirety, and to U.S. Application No. 62/678,622, filed on May 31, 2018, which is incorporated herein by reference in its entirety.

STATEMENT REGARDING FEDERALLY SPONSORED RESEARCH

This invention was made with government support from grant P01NS045260 from NINDS, R01NS057128 from NINDS, and R15MH101703 from NIMH. The government has certain rights in the invention.

FIELD OF THE INVENTION

The invention relates to compositions and methods for treating neurodevelopmental disorders and neuropsychiatric and neurological diseases by regulating p18.

BACKGROUND

The mechanistic target of rapamycin (mTOR) is a highly conserved and ubiquitously expressed protein kinase complex, which plays important roles in cell survival, growth, and metabolism. mTOR, consists of two complexes, mTORC1 and mTORC2, which integrate extracellular signals (growth factors, neurotransmitters, nutrients, etc.) with intracellular energy levels and cellular stress status to regulate many important cellular functions (Laplante & Sabatini, 2012; Takei & Nawa, 2014). Abnormal mTOR signaling has been implicated in various neurodevelopmental disorders and neuropsychiatric and neurological diseases (Costa-Mattioli & Monteggia, 2013). Recent evidence indicates that amino acid-induced lysosomal recruitment of mTORC1 is essential for its full activation (Jewell et al., 2013). In the presence of amino acids, mTORC1 is activated by binding to heterodimers consisting of the Rag small guanosine triphosphatases (GTPases), RagA and RagB in their GTP-bound states, and RagC and RagD in their GDP-bound states (Ham et al., 2016). Lysosomal localization of Rag dimers is maintained through their binding to the Ragulator complex, which consists of p18 (also known as LAMTOR1), p14 (LAMTOR2), MP1 (LAMTOR3), C7orf59 (LAMTOR4), and HBXIP (LAMTOR5) proteins (Bar-Peled et al., 2012; Nada et al., 2009; Sancak et al., 2010); acylation of p18 is essential for anchoring the Ragulator complex to endosomal/lysosomal membranes (Nada et al., 2009).

Although it has been shown that lysosomal localization and interaction with Rag GTPases are essential for p18 to regulate mTORC1 activation (Sancak et al., 2010), little is known regarding the regulation of p18 levels. A previous study combining single-step immuno-enrichment of ubiquitinated peptides with high-resolution mass spectrometry revealed that p18 was ubiquitinated at residues K20 and K31 in HEK cells and MV4-11 cells (Wagner et al., 2011). However, the E3 ligase responsible for p18 ubiquitination was not identified. Furthermore, whether the Ragulator-Rag complex regulates mTORC1 in central nervous system (CNS) in a way similar to that in peripheral tissues is not known.

UBE3A, an E3 ligase in the ubiquitin-proteasomal system, plays important roles in brain development and normal function, as UBE3A deficiency results in Angelman syndrome (AS) (Williams et al., 1990), while UBE3A overexpression increases the risk for autism (Cook et al., 1997). It has been reported that imbalanced signaling of the mTOR pathway, with increased mTORC1 and decreased mTORC2 activation, plays important roles in the motor dysfunction and abnormal dendritic spine morphology of Purkinje neurons in AS mice (Sun et al., 2015a). A similar abnormal mTOR signaling is critically involved in Ube3a deficiency-induced impairment in hippocampal synaptic plasticity and fear-conditioning memory (Sun et al., 2016). Furthermore, inhibition of mTORC1 by rapamycin treatment not only reduced mTORC1 activity but also normalized mTORC2 activity, suggesting that mTORC1 overactivation is the trigger for alterations in mTOR signaling in AS mice. However, how Ube3a deficiency results in mTORC1 overactivation remains unknown. As described below, the potential regulation of p18 levels by Ube3a were investigated. Ube3a directly ubiquitinates p18 and targets it for proteasomal degradation, which normally limits mTORC1 signaling and activity-dependent synaptic remodeling. In the absence of Ube3a, p18 accumulates in neurons, resulting in mTORC1 overactivation, abnormal synaptic morphology, and impaired synaptic plasticity and learning. These findings reveal a previously unidentified regulatory mechanism for mTORC1 activation and suggest potential therapeutic targets for cognitive disorders associated with abnormal mTORC1 signaling.

SUMMARY OF THE INVENTION

The invention generally relates to compositions and methods for treatment of neurological disorders.

In one aspect, the invention relates to inhibitory RNAs that reduce the expression of p18, and viral vectors encoding such inhibitory RNAs. The invention also relates to pharmaceutical compositions containing the inhibitory RNAs and viral vectors encoding the inhibitory RNAs. The invention also relates to methods of treatment for neurological disorders, including Angelman Syndrome, Autism Spectrum Disorder, epilepsy, Tuberous Sclerosis Complex, Focal Cortical Dysplasia, and Fragile X syndrome, by administering to patients in need of such treatment an inhibitory RNA that reduces expression of p18.

In another aspect, the invention relates to inhibitory fusion peptides that disrupt the interaction between p18 and Ube3a. Inhibitory fusion peptides of the invention include a short polypeptide sequence from p18 and a cell penetrating peptide. The invention also relates to pharmaceutical compositions containing such inhibitory fusion peptides. The invention also relates to methods of treatment for neurological disorders, including Angelman Syndrome, Autism Spectrum Disorder, epilepsy, Tuberous Sclerosis Complex, Focal Cortical Dysplasia, and Fragile X syndrome, by administering to patients in need of such treatment an inhibitory fusion peptide that disrupts the interaction between p18 and Ube3a.

Figure 1:
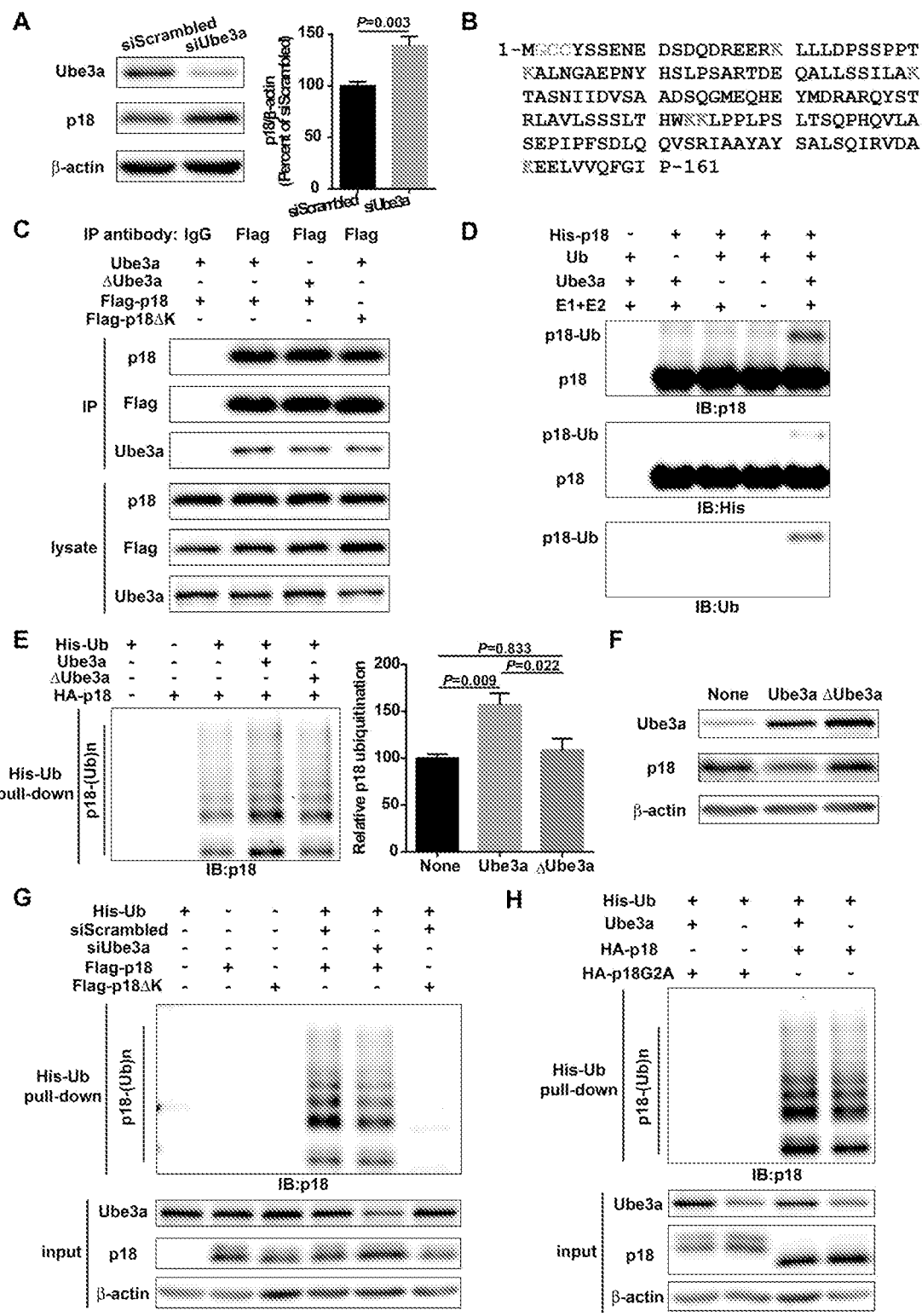
FIG. 1(A-H) shows that P18 is a Ube3a substrate. (A) Western blot analysis using anti-Ube3a, p18, or β-actin antibodies of lysates from COS-1 cells transfected with scrambled siRNA or Ube3a siRNA. Right, quantitative analysis of blots. N=6 independent experiments, p=0.003 (unpaired, two-tailed Student's t test). (B) Amino acid sequence of human p18 (SEQ ID NO: 23). G2 is a myristoylation site. C3 and C4 are palmitoylation sites. K20, K31, K60, K103, K104, and K151 are potential ubiquitination sites. (C) Interaction between p18 and Ube3a. Lysates from COS-1 cells transfected with the indicated cDNAs in expression vectors were immunoprecipitated with an anti-Flag antibody or control IgG and probed with the indicated antibodies. The presence of Flag-p18 in precipitates was confirmed with anti-p18 and anti-Flag antibodies. (D) In vitro ubiquitination of p18 by recombinant Ube3a. Reaction products were analyzed by Western blots with p18, His, and ubiquitin antibodies. Note that the p18-Ub band is present only when all reaction elements were added. € Overexpression of Ube3a, but not ΔUbe3a, enhances p18 ubiquitination in COS-1 cells. His-tagged ubiquitinated proteins in cells co-transfected with HA-p18 plus empty vectors (None, but with endogenous Ube3a), wild-type Ube3a (Ube3a), or its inactive form Ube3a-C833A (ΔUbe3a) were precipitated using Talon resin and probed with anti-p18 antibodies. Ubiquitinated p18 proteins are labeled with "p18-(Ub)n". Right, quantification of the relative abundance of ubiquitinated p18 (means±SEM, p=0.009 None vs Ube3a, p=0.022 Ube3a vs ΔUbe3a, p=0.833 None vs ΔUbe3a, n=3 independent experiments, one-way ANOVA with Tukey's post hoc analysis). (F) Western blot analysis using anti-Ube3a, p18 or β-actin antibodies on lysates from COS-1 cells transfected with empty vector, Ube3a, or ΔUbe3a vectors. (G) siRNA knock-down of Ube3a in COS-1 cells reduces p18 ubiquitination. COS-1 cells were incubated with Ube3a siRNA or scrambled control siRNA 48 h before transfection with Flag-p18 or Flag-p18ΔK and His-ubiquitin. Twenty-four h later, ubiquitinated proteins were isolated by $Co^{2+}$-affinity chromatography. Levels of ubiquitinated p18 protein (p18-(Ub)n, upper panel) were determined by Western blots. Levels of input proteins were also evaluated by Western blots probed with Ube3a, p18, and β-actin antibodies (lower panel). (H) His-ubiquitin pull down assay performed using HA-p18 or HA-p18G2A. Upon purification, levels of ubiquitinated p18 (upper panel) were determined by Western blot analysis. Lower panel, input of Ube3a, p18, and β-actin. See also FIG. 9.

(B) Effects of p18 downregulation in hippocampal CA1 region on the proportion of various spine types in WT and AS mice. (C) % freezing for different experimental groups in tone memory (means±S.E.M. of 6-10 mice; p=0.960, WT-siScrambled vs WT-siP18; p<0.001, WT-siScrambled vs AS-siScrambled; p=0.477, AS-siScrambled vs AS-siP18, two-way ANOVA with Tukey's post-hoc analysis).

FIG. 18 shows bilateral intra-hippocampal injection of AAV-siRNA p18 targeting field CA1 selectively affected context learning in WT and AS mice (impairment in WT and improvement in AS mice). Left panel: % freezing for different experimental groups in context memory (means±S.E.M. of 6-10 mice; p=0.043, WT-siScrambled vs WT-siP18; p<0.001, WT-siScrambled vs AS-siScrambled; p<0.001, AS-siScrambled vs AS-siP18, two-way ANOVA with Tukey's post-hoc analysis). Right panel: % freezing for different experimental groups in cue memory (means±S.E.M. of 6-10 mice; p=0.960, WT-siScrambled vs WT-siP18; p<0.001, WT-siScrambled vs AS-siScrambled; p=0.477, AS-siScrambled vs AS-siP18, two-way ANOVA with Tukey's post-hoc analysis).

FIG. 19 shows Bilateral intra-hippocampal injection of AAV-siRNA p18 targeting field CA1 reduced ARC expression more in WT than in AS mice. Upper panels: Representative images of CA1 pyramidal neurons stained with anti-ARC (red) and -GFP (green) antibodies. Scale bar=50 μm (low power images) and 10 μm (high power images). Lower panel: Quantitative analysis of the mean fluorescence intensity (MFI) of ARC-immunoreactivity of CA1 pyramidal neurons (means±S.E.M. of 3 slices from 3 different animals; p<0.001, WT-siScrambled vs WT-siP18; p=0.017, WT-siScrambled vs AS-siScrambled; p<0.001, AS-siScrambled vs AS-siP18; p=0.016, WT-siP18 vs AS-siP18, two-way ANOVA with Tukey's post-hoc analysis).

FIG. 20(A-C) shows effects of p18 short peptides on lysosome positioning and mTOR signaling. (A) Amino acid sequence of human p18 (SEQ ID NO: 23). G2 is a myristoylation site. C3 and C4 are palmitoylation sites. K20, K31, K60, K103, K104, and K151 (red) are potential ubiquitination sites. Two short peptides around K20/31 and K151 (underlined) were respectively conjugated to the cell membrane transduction domain of HIV-1 Tat protein (TAT-2031 and TAT-151). (B) TAT-2031 treatment shifted the distribution of lysosomes toward the cell periphery. Hela cells were stained with Lysotracker (red) and imaged live. Top panel, representative images of Lysotracker before and 30 min after TAT-2031 treatment are shown. Bottom panel, graph represents the distribution of lysosomes relative to the MTOC, normalized to the distance between the MTOC and the cell periphery. (C) Hela cells were incubated with TAT or TAT-2031 (2 μM) for 42 hr. Representative blots and quantification of p18, p-mTOR/mTOR, p-S6K1/S6K1, and p-S6/S6 in whole cell lysates are shown. N=2 independent experiments.

FIG. 21(A-D) shows that P18 regulates dendritic trafficking and positioning of lysosomes in cultured mouse hippocampal neurons. (A) Primary hippocampal neurons (DIV7+14) were infected with viral vectors containing either p18 shRNA (shP18) or scrambled shRNA (shSc) and GFP (green). They were stained with LysoTracker (Red), and live imaged every second for 1 min to visualize lysosomal trafficking in dendrites. Dendrite segments and kymographs of dendritic movement of LysoTracker-labeled vesicles. Scale bar represents 20 μm. (B) Quantitative analysis of vesicle movement from kymographs. Vesicles were manually classified according to their movement in a blinded fashion. N=40 neurons from 7 independent experiments for Scrambled and 41 neurons from 7 independent experiments for p18 KD, two-way ANOVA with Tukey's post-test. (C) Quantification of the overall percent of lysosome moving in anterograde vs. retrograde direction. N=12 neurons from 3 independent experiments for Scrambled and 13 neurons from 3 independent experiments for p18 KD, two-way ANOVA with Sidak's post-test. (D) Quantification of lysosome distribution along the proximal dendrites (1=65 μm). N=3 neurons from 3 independent experiments, two-way ANOVA with Sidak's post-test.

DETAILED DESCRIPTION

The invention generally relates to compositions and methods for treatment of neurological disorders. Abnormal mTORC1 activation has been implicated in several developmental neurological disorders. As shown below, Ube3a regulates mTORC1 signaling by targeting p18, a subunit of the Ragulator. Ube3a ubiquitinates p18, resulting in its proteasomal degradation, and Ube3a deficiency in the hippocampus of AS mice induces increased lysosomal localization of p18 and other members of the Ragulator-Rag complex, and increased mTORC1 activity. p18 knockdown in hippocampal CA1 neurons of AS mice reduces elevated mTORC1 activity and improves dendritic spine maturation, long-term potentiation (LTP), as well as learning performance. The examples, below, indicate that Ube3a-mediated regulation of p18 and subsequent mTORC1 signaling is critical for typical synaptic plasticity, dendritic spine development, and learning and memory. An object of the invention is to inhibit the function of p18 either by inhibition or reduction of p18 expression or inhibition or reduction of p18 binding to Ube3a.

One embodiment of the invention is an inhibitory RNA comprising an RNA oligonucleotide that reduces the expression of p18. In some embodiments, an inhibitory RNA of the invention may be an shRNA, siRNA, or sgRNA. RNA interference (RNAi) is a natural process through which expression of a targeted gene can be knocked down with high specificity and selectivity. Small interfering RNA (siRNA), well-known in the art, are double stranded RNA with 2 nucleotide 3' end overhangs that activate RNAi, leading to the degradation of mRNAs in a sequence-specific manner dependent upon complementary binding of the target mRNA. As known in the art, siRNAs may be manufactured by directly synthesizing an siRNA in a test tube and then introducing it into a cell via transfection, or by introducing an siRNA expression vector which is manufactured to express siRNAs in a cell or a PCR-derived siRNA expression cassette into a cell via transfection or infection, or the like. The method of synthesizing an siRNA and introducing it into a cell or an animal may vary depending on the purpose of an experiment or the cellular/biological functions of a gene product.

Short hairpin RNAs (shRNA), also well-known in the art, contain a loop structure that is processed to siRNA and also leads to the degradation of mRNAs in a sequence-specific manner dependent upon complementary binding of the target mRNA.

In the mechanism of CRISPR/Cas9, sgRNA, or single guide RNA, as known in the art, directs the Cas9 nuclease to its target DNA. Cas9 creates a double-strand break in the DNA, which the cell repairs using one of its natural mechanisms often resulting in insertions or deletions that generates gene knockouts.

Preferably, inhibitory RNAs of the invention comprise a nucleotide sequence complementary to a partial coding sequence for p18. For an inhibitory RNA of the invention, wherein said RNA is shRNA, the shRNA comprises an RNA sequence with at least 80%, at least 85%, at least 90%, at least 95%, or 100% complementarity to SEQ ID NO:1 or SEQ ID NO:2. For an inhibitory RNA, wherein said RNA is siRNA, the siRNA comprises an RNA sequence with at least 80%, at least 85%, at least 90%, at least 95%, or 100% complementarity to SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16. For an inhibitory RNA of the invention, wherein said RNA is sgRNA, the sgRNA comprises an RNA sequence with at least 80%, at least 85%, at least 90%, at least 95%, or 100% complementarity to SEQ ID NO:17, or SEQ ID NO:18. The inhibitory RNAs according to the invention include RNAs with modifications such as a substitution, an insertion, a deletion, or a combination thereof, in which the change does not decrease the activity of the inhibitory RNA.

Inhibitory RNAs of the invention may be used in any cell where p18 is expressed in order to suppress the expression of the p18 protein by at least 50%. In some embodiments, an inhibitory RNA of the invention completely inhibits expression of the p18 protein. In other embodiments, an inhibitory RNA of the invention reduces the expression of the p18 protein. An effective amount of an inhibitory RNA of the invention is the amount for obtaining the intended result, for example, the amount sufficient for providing a reduced level of the expression of p18 gene compared to the normal expression detected in the absence of the RNA. An inhibitory RNA of the invention may be introduced in an amount which may allow the delivery of at least a single copy per each cell. The greater the amount of copies (for example, 5 or more copies, 10 or more copies, 100 or more copies, or 1,000 or more copies per each cell, respectively), the higher the inhibition efficiency, and one with a lesser amount of introduction may be more advantageous in a particular application.

Administration of inhibitory RNAs of the invention may be performed by a known method by which a nucleic acid is introduced into a target cell in vivo or in vitro. The method of introducing the inhibitory RNA into a cell is not particularly limited. Preferably, the inhibitory RNA may be directly sunk into a host cell, or introduced after transfecting the host cell using a viral vector. The viral vector to be used is not particularly limited. The viral vector that encodes for and expresses an inhibitory RNA of the invention may include a plasmid or a viral vector, for example, an adeno-associated virus, a retrovirus, a vaccinia virus, and an oncolytic virus. Meanwhile, a conventional gene transfer technology may include transfection using calcium phosphate, DEAE-dextran, electroporation, and microinjection, and viral vector. Commercially available products such as Accell siRNA (Dharmacon GE) use siRNA modifications to allow for passive uptake to achieve knockdown.

Another embodiment of the invention is a viral vector encoding an inhibitory RNA of the invention. Commercial methods to introduce inhibitory RNAs into viral vectors are available. For example Vector Biolabs provides a custom adeno-associated virus (AAV) production service which begins with subcloning the gene or RNA of interest into a related pAAV, followed by large scale preparation of the pAA cis-plasmid and complimentary plasmids using Qiagen Endo-free Mega Prep kits, followed by large-scale transfection of involved plasmids into HEK293 cells, ending with harvesting the AAV production cells and purifying the AAVs through a series of CsCl centrifugations. Protocols for package of lenti-shRNA virus using HEK293T cells known in the art. See e.g., https://www.mdanderson.org/documents/core-facilities/Functional %20Genomics %20Core/Lentivirus %20production %20protocols.pdf (accessed May 28, 2019). For in vivo applications the AAV viral vector encoding an inhibitory RNAs of the invention is particularly preferred.

The invention also provides for an inhibitory fusion polypeptide that disrupts the interaction between p18 and Ube3a. An inhibitory fusion polypeptide of the invention comprises a polypeptide comprising an amino acid sequence with at least 90%, at least 95%, or 100% sequence identity to SEQ ID NO:19; and a cell penetrating polypeptide. Surprisingly, as shown in Example 9, the short decoy peptide around K20/31, but not the peptide around K151, significantly reduced mTORC1 activation and increased lysosome distribution to the peripheral region of the cell.

Several cell penetrating peptides are known in the art, for example, HIV-1 TAT, penatratin, polyarginines, DPV1047, MPG, Pep-1, pVEC, ARF (1-22), BPrPr (1-28), MAP, Transportan, p28, VT5, Bac 7, C105Y, PFVYLI, and Pep-7. See Guidotti et al., Trends in Pharmacological Sciences, 38:406-424 (2017). Preferably, the cell penetrating peptide is a TAT peptide as set forth in SEQ ID NO: 20.

The invention also relates to pharmaceutical compositions. Pharmaceutical compositions of the invention comprise an inhibitory RNA of the invention, a viral vector encoding an inhibitory RNA of the invention, or an inhibitory fusion polypeptide of the invention. Pharmaceutical compositions of the invention may further include a pharmaceutically acceptable carrier or excipient. Pharmaceutically acceptable excipients are widely known in the related art, and are relatively inert materials that help in the easy administration of a pharmaceutically active material. For example, an excipient may provide a shape or a viscosity, and may serve as a diluent. Examples of a suitable excipient may include a stabilizing agent, a humectant, an emulsifier, salts that can change osmolarity, an encapsulant, a buffer solution, but are not limited thereto. Excipients and formulations for parenteral drug delivery are provided in the art. (Remington, The Science and Practice of Pharmacy 20th edition, Mack Publishing (2000).

In another aspect, the invention relates to methods of treatment of a neurological disorder. In one embodiment, a method of treatment of a neurological disorder comprises administering to a subject in need thereof, an inhibitory RNA of the invention, a viral vector encoding an inhibitory RNA of the invention, or a pharmaceutical composition comprising an inhibitory RNA of the invention, a viral vector encoding an inhibitory RNA of the invention, wherein the neurological disorder is selected from the group consisting of Angelman Syndrome, Autism Spectrum Disorder, epilepsy, Tuberous Sclerosis Complex, Focal Cortical Dysplasia, and Fragile X syndrome.

In another embodiment, a method of treatment of a neurological disorder comprises administering to a subject in need thereof, an inhibitory fusion polypeptide of the invention, or a pharmaceutical composition comprising an inhibitory fusion polypeptide of the invention, wherein the neurological disorder is selected from the group consisting of Angelman Syndrome, Autism Spectrum Disorder, epilepsy, Tuberous Sclerosis Complex, Focal Cortical Dysplasia, and Fragile X syndrome.

In the methods of treatment according to the invention, administering refers to the introduction of a particular material to a patient in any appropriate way, and the administration of a substance may be performed via a general route as long as it can be arrived at the target tissue. One method of administration is via intrathecal injection into the spinal canal. Intrathecal formulations are sterile isotonic solutions. In some methods intrathecal administration may be performed using a pump. An intrathecal formulation requires chemical, physical, and thermal stability under all conditions associated with intrathecal delivery via an external or implantable pump. Further, biological activity must not be decreased through surface adsorption upon incubation. Formulations appropriate for intrathecal delivery must also contain a sufficient amount of biologically acceptable salt to maintain fluid tonicity. Preferably, a formulation contains sufficient salt to be isotonic, within physiologically acceptable limits, with human blood or cerebral spinal fluid. A preferred salt is sodium chloride (NaCl), but other biologically acceptable salts may be used, such as potassium chloride, calcium chloride, and magnesium chloride. The salt may be one salt or a combination of salts.

In methods of treatment according to the invention which require administration of viral vectors, several options are available. In one method of treatment, viral vectors are packaged in liposomes in addition to focused ultrasound-induced blood brain-barrier opening, as described in Lin C Y et al., 2019. In another method AAV capsids are used to facilitate efficient and noninvasive gene transfer to the central and peripheral nervous systems, as described by Challis R C et al., 2019. In another method of treatment the invention, gene transfer to rat cerebral cortex is mediated by polysorbate 80 and poloxamer 188 nonionic surfactant vesicles, as in Attia N et al., 2018. In yet another method of treatment of the invention, blood brain barrier-crossing antibodies, brain-tropic adenoviral vectors and engineered extracellular vesicles are used to administer viral vectors to the neurological tissue. See e.g, Stanimirovic et al., BioDrugs (2018) 32:547-559, FIG. 1.

Methods of treatments of the invention may be directed to various neurological disorders. The overactivation of mTOR has been implicated in the pathogenesis of syndromic autism spectrum disorder (ASD), such as tuberous sclerosis complex (TSC). Treatment with the mTOR inhibitor rapamycin improved social interaction deficits in mouse models of TSC. Kotajima-Murakami et al. 2019. A broad spectrum of malformations of cortical development, such as focal cortical dysplasia (FCD) and tuberous sclerosis complex (TSC), have been linked to either germline or somatic mutations in mTOR pathway-related genes, commonly summarised under the umbrella term 'mTORopathies'. Muhlebner A, et al. (2019). Constitutive activation of mTOR signalling represents a shared pathogenic mechanism in a group of developmental malformations that have histopathological and clinical features in common, such as epilepsy, autism and other comorbidities. A. Muhlebner, et al. (2019).

Materials and Methods

Animals. Animal experiments were conducted in accordance with the principles and procedures of the National Institutes of Health Guide for the Care and Use of Laboratory Animals. All protocols were approved by the local Institutional Animal Care and Use Committee. Original Ube3a mutant (AS) mice were obtained from The Jackson Laboratory, strain B6.12957-Ube3atm1Alb/J, and a breeding colony was established, as previously described (Baudry et al., 2012). In all experiments male AS mice aged between 2-4 months were used. Control mice were age-matched, male, wild-type littermates. Mice, housed in groups of two to three per cage, were maintained on a 12-h light/dark cycle with food and water ad libitum.

Hippocampal Neuronal Cultures. For neuronal culture preparations, wild-type (WT) or Ube3am−/p+ female and WT male mice were used for breeding. Hippocampal neurons were prepared from E18 mouse embryos as described (Sun et al., 2015b). Briefly, hippocampi were dissected and digested with papain (2 mg/ml, Sigma) for 30 min at 37° C. Dissociated cells were plated onto poly-D-lysine-coated 6-well plate at a density of 6-10×104 cells/cm2 or coverslips in 24-well plate at a density of 6-10×$10^2$ cells/cm' in Neurobasal medium (GIBCO) supplemented with 2% B27 (GIBCO) and 2 mM glutamine and kept at 37° C. under 5% $CO_2$. Half of the culture medium was replaced with fresh culture medium at DIV4 and then every 7 days. Genotyping was carried out by polymerase chain reaction (PCR) of mouse tail DNA as described previously (Baudry et al., 2012).

Cell Lines. COS-1 cells (ATCC) were grown in DMEM supplemented with 10% (vol/vol) fetal bovine serum (FBS) (Invitrogen) and kept at 37° C. under 5% CO2.

Transfection and Lentiviral Infection. For transient expression of constructs, COS-1 cells were transfected with the respective constructs by lipofection (Lipofectamine 2000; Invitrogen) according to the manufacturer's instructions. Small interfering RNA (siRNA) transfections were also performed with Lipofectamine 2000. Cells were incubated with 10 or 20 nM SMARTpool siRNA duplexes against human UBE3A, or a scrambled duplex (Dharmacon) for 72 h before downstream analysis.

Cultured hippocampal neurons from WT mice were infected with p18 shRNA (mouse) lentivirus (sc-108727-V, Santa Cruz Biotechnology) or scrambled shRNA lentivirus (sc-108080, Santa Cruz Biotechnology), and co-transfected with Accell Ube3a siRNA (GE Dharmacon) or Accell Non-targeting siRNA (GE Dharmacon) at DIV 4, and 24 h after infection, ⅔ medium was replaced with fresh medium. Cultured neurons were used 3 days after infection.

Cultured WT and AS hippocampal neurons were infected with p18 shRNA (mouse) lentivirus (sc-108727-V, Santa Cruz Biotechnology) or scrambled shRNA lentivirus (sc-108080), together with copGFP control lentivirus (as an infection marker, sc-108084) at DIV 14, and 24 h after infection, ⅔ medium was replaced with fresh medium. Neurons were analyzed 8 days after infection.

Cultured WT and AS hippocampal neurons were infected with p18 shRNA (mouse) AAV (custom, VectorBuilder) or scrambled shRNA AAV (custom, VectorBuilder) at DIV 7, and 24 h after infection, ⅔ medium was replaced with fresh medium. Neurons were analyzed 14 days after infection.

Antibodies, chemicals, and plasmids used in this study are listed in Table 1. All antibodies listed were validated for Western blot and/or immunohistochemistry by their respective sources. Further validation was performed for each IHC-recommended antibody following the Rimm Lab Algorithm (Bordeaux et al., 2010).

P2/S2 Fractionation, Lysosomal Fractionation, and Western Blot Analysis. P2/S2 fractionation were performed according to published protocols (Sun et al., 2015a). Briefly, frozen hippocampus tissue was homogenized in ice-cold HEPES-buffered sucrose solution (0.32 M sucrose, 4 mM HEPES, pH 7.4) with protease inhibitors. Homogenates were centrifuged at 900 g for 10 min to remove large debris (P1). The supernatant (S1) was then centrifuged at 11,000×g for 20 min to obtain crude membrane (P2) and cytosolic (S2) fractions. P2 pellets were sonicated in RIPA buffer (10 mM Tris, pH 8, 140 mM NaCl, 1 mM EDTA, 0.5 mM EGTA, 1% NP-40, 0.5% sodium deoxycholate, and 0.1% SDS). For whole homogenates, tissue was homogenized in RIPA buffer. Protein concentrations were determined with a BCA protein assay kit (Pierce).

Lysosome-enriched fractions were prepared from cultured neurons or isolated hippocampus using the lysosome enrichment kit (Pierce). The purity of the fractions was assessed using antibodies against cathepsin B (lysosomes) and COXIV (mitochondria). Cultured hippocampal neurons from WT mice were transfected with Accell p18 siRNA or Accell Non-targeting siRNA (GE Dharmacon) at DIV 7, and were used 4 days after transfection. At least three independent experiments were performed.

Western blots were performed according to published protocols (Sun et al., 2015b). Briefly, samples were separated by SDS-PAGE and transferred onto a PVDF membrane (Millipore). After blocking with 3% BSA for 1 h, membranes were incubated with specific antibodies overnight at 4° C. followed by incubation with secondary antibodies (IRDye secondary antibodies) for 2 h at room temperature. Antibody binding was detected with the Odyssey® family of imaging systems.

Immunoprecipitation and Denaturing Immunoprecipitation. For immunoprecipitation, all procedures were carried out at 4° C. COS-1 cells transfected with the indicated cDNAs or cultured hippocampal neurons were lysed with lysis buffer (Tris-HCl 25 mM pH 7.4, NaCl 150 mM, 1 mM EDTA, 1% NP-40, 5% glycerol and a protease inhibitor cocktail). After a brief centrifugation to remove insoluble material, the supernatant was precleared with an aliquot of agarose beads. For immunoprecipitation of Flag-p18 or Flag-p18ΔK in COS-1 cells, extracts were incubated overnight with anti-Flag agarose beads, washed with lysis buffer, followed by elution of bound proteins by heating at 95° C. for 10 min in SDS-PAGE sample buffer. For immunoprecipitation of p18 in hippocampal neurons, extracts were incubated with anti-p18 antibodies overnight and immunoprecipitates were collected with protein A/G Agarose. For immunoprecipitation of RagA in mouse hippocampus, rabbit anti-RagA antibodies were incubated with hippocampal lysates and precipitated with Protein A/G-conjugated beads. Inputs and precipitates were resolved by SDS-PAGE and analyzed by Western blotting. All studies were performed in 3-5 independent experiments.

For immunoprecipitation of ubiquitin from hippocampal crude membrane fractions under denaturing conditions, P2 pellets were resuspended and heated in denaturing lysis buffer (1% SDS, 50 mM Tris, pH 7.4, 5 mM EDTA, 10 mM DTT, 1 mM PMSF, 2 µg/ml leupeptin, 15 U/ml DNase I) and diluted in 9 volumes of ice-cold non-denaturing lysis buffer (1% Triton X-100, 50 mM Tris, pH 7.4, 300 mM NaCl, 5 mM EDTA, 10 mM iodoacetamide, 1 mM PMSF, 2 µg/ml leupeptin). Lysates were centrifuged at 16,000×g for 30 min at 4° C. and cleared with protein A/G Agarose beads. Pre-cleared lysates were then incubated with anti-ubiquitin antibodies coupled to protein A/G Agarose beads overnight at 4° C., followed by four washes with ice-cold wash buffer (0.1% Triton X-100, 50 mM Tris, pH 7.4, 300 mM NaCl, 5 mM EDTA) and elution in 2×SDS sample buffer. Immunoprecipitated proteins were resolved by SDS-PAGE followed by Western blot analysis with specific antibodies against p18 and ubiquitin. Relative p18 ubiquitination refers to the ratio of ubiquitinated p18 over total p18, and was normalized to the average value of the WT group. At least three independent experiments were performed.

In Vitro Ubiquitin Assay. His-p18 proteins were purchased from CUSABIO (Wuhan, China). For in vitro ubiquitination experiments, we used the E6AP (UBE3A) Ubiquitin Ligase Kit (Boston Biochem), following the manufacturer's instruction. Briefly, purified His-p18 proteins were incubated for 90 min at 37° C. under constant shaking with E1 enzyme, E2 enzyme (UBE2L3), His6-E6AP, ubiquitin, $Mg^{2+}$-ATP, and Reaction Buffer. The reaction was terminated by the addition of SDS sample buffer, and samples were boiled, and proteins separated with 14% SDS-PAGE. Blots were probed with p18, ubiquitin, and His antibodies. At least three independent experiments were performed.

His-ubiquitin Pull-down Assay. COS-1 cells in 60 mm dishes were transfected with 2.5 µg His-ubiquitin, 2.5 µg HA-p18 or HA-p18G2A, and 5 µg HA-Ube3a or HA-Ube3a C833A constructs in the indicated combinations. Ube3a siRNA-treated COS-1 cells were transfected with 2.5 µg Flag-p18 or p18ΔK and 2.5 µg His-ubiquitin 48 h after siRNA treatment. Twenty-four hours after transfection, cells were lysed, and His-ubiquitin-conjugated proteins were purified as described (Sun et al., 2015b). Briefly, cells were harvested in 1 ml of ice-cold phosphate-buffered saline, and the cell suspension was divided into two parts; 100 µl were lysed using 1×SDS-PAGE sample loading buffer containing 10% DTT, and 900 µl were lysed in Buffer A (6 M guanidine HCl, 0.1 M $Na_2HPO_4/NaH_2PO_4$, 0.5 M NaCl, 10 mM imidazole, 0.1% Nonidet P-40, and 5% glycerol, pH 8.0) and sonicated. The guanidine lysates were incubated with 30 µl of equilibrated Talon resin at 4° C. for 4 h to bind His-tagged ubiquitinated proteins. Beads were then washed one time with Buffer A, followed by four washes with Buffer B (8 M urea, 0.1 M Na2HPO4/NaH2PO4, 0.5 M NaCl, 20 mM imidazole, 0.1% Nonidet P-40, and 5% glycerol, pH 8.0). The protein conjugates were eluted in 30 µl of 2× laemmli/imidazole (200 mM imidazole) and boiled. Eluates were analyzed by Western blotting using either p18 or ubiquitin antibody. At least three independent experiments were performed.

Acute Hippocampal Slice Preparation. Adult male mice (2-4-month-old) were anesthetized with gaseous isoflurane and decapitated. Brains were quickly removed and transferred to oxygenated, ice-cold cutting medium (in mM): 124 NaCl, 26 $NaHCO_3$, 10 glucose, 3 KCl, 1.25 $KH_2PO_4$, 5 $MgSO_4$, and 3.4 $CaCl_2$. Hippocampal transversal slices (400 µm-thick) were prepared using a McIlwain-type tissue chopper and transferred to i) an interface recording chamber and exposed to a warm, humidified atmosphere of 95% $O_2$/5% $CO_2$ and continuously perfused with oxygenated and preheated (33±0.5° C.) artificial cerebrospinal fluid (aCSF) (in mM) [110 NaCl, 5 KCl, 2.5 $CaCl_2$, 1.5 $MgSO_4$, 1.24 $KH_2PO_4$, 10 D-glucose, 27.4 $NaHCO_3$], perfused at 1.4 ml/min (electrophysiology); or ii) a recovery chamber with a modified aCSF medium, containing (in mM): 124 NaCl, 2.5 KCl, 2.5 $CaCl_2$, 1.5 $MgSO_4$, 1.25 $NaH_2PO_4$, 24 $NaHCO_3$, 10 D-glucose, and saturated with 95% $O_2$/5% $CO_2$ for 1 h at 37° C. (biochemical assays).

Electrophysiology. After 1.5 h incubation at 33±0.5° C. in the recording chamber, a single glass pipette filled with 2 M NaCl was used to record field EPSPs (fEPSPs) elicited by stimulation of the Schaffer collateral pathway with twisted nichrome wires (single bare wire diameter, 50 µm) placed in CA1 stratum radiatum. Stimulation pulses were generated using a Multichannel Systems Model STG4002 Stimulator (Reutlingen, Germany). Responses were recorded through a differential amplifier (DAM 50, World Precision Instruments, USA) with a 10-kHz high-pass and 0.1-Hz low-pass filter. Before each experiment, the input/output (I/O) relation was examined by varying the intensity of the stimulation. Paired-pulse facilitation was tested at 20-300 ms interval.

Long-term potentiation (LTP) was induced using theta burst stimulation (10 bursts at 5 Hz, each burst consisting of 4 pulses at 100 Hz, with a pulse duration of 0.2 ms). For LTP and paired-pulse facilitation experiments, the stimulation intensity was regulated to a current which elicited a 40% of maximal response. Data were collected and digitized by Clampex, and the slope of fEPSP was analyzed. MHY1485 (2 µM) was applied to slices for 60 min before theta-burst stimulation (TBS). Some of the slices were processed for Western blots. All data are expressed as means±SEM, and statistical significance of differences between means was calculated with appropriate statistical tests as indicated in figure legends.

Whole-cell patch-clamp recording was performed as previously described (Vogel-Ciernia et al., 2013). Briefly, hippocampal slices were prepared on the horizontal plane at a thickness of 370 µm from 2 to 4-month-old male mice with a Leica vibrating tissue slicer (Model: VT1000S). Slices were placed in a submerged recording chamber and continuously perfused at 2-3 mL/min with oxygenated (95% $O_2$/5% $CO_2$) at 32° C. Whole-cell recordings (Axopatch 200A amplifier: Molecular Devices) were made with 4-7 MO recording pipettes filled with a solution containing (in mM): 130 $CsMeSO_4$, 10 CsCl, 8 NaCl, 10 HEPES, 0.2 EGTA, 5 QX-314, 2 Mg-ATP, 0.3 Na-GTP. Osmolarity was adjusted to 290-295 mOsm and pH 7.4. Spontaneous mEPSCs were recorded at a holding potential of −70 mV in the presence of tetrodotoxin (1 µM) and picrotoxin (50 µM). Data were filtered at 2 kHz, digitized at 1-5 kHz, stored on a computer, and analyzed off-line using Mini Analysis Program (Synaptosoft), Origin (OriginLab) and pCLAMP 7 (Molecular Devices) software. Statistical significance was determined by pooling events from cells of the same genotype and running a Student's t test on the pooled data. $P<0.05$ was considered statistically significant.

Immunofluorescence. Cultured hippocampal neurons were fixed in 2% paraformaldehyde (PFA)/10% sucrose for 15 min at 37° C., transferred to 0.05% Triton X-100/PBS for 5 min at 4° C., and then 0.02% Tween-20/PBS for 2 min at 4° C. Coverslips were washed twice with ice cold PBS and incubated 1 h in 3% BSA/PBS at room temperature. For staining of F-actin, Rhodamine-Phalloidin (Invitrogen) was incubated in 1% BSA/PBS overnight at 4° C. For staining of p18, LAMTOR4, RagA, LAMP2, and MAP2, cells were incubated with rabbit anti-p18 (1:200, Sigma), rabbit anti-LAMTOR4 (1:500, CST), rabbit anti-RagA (1:100, CST), rat anti-LAMP2 (1:200, Abcam), mouse anti-MAP2 (1:500, Abcam) respectively in 3% BSA/PBS overnight at 4° C. Coverslips were then washed twice with ice cold PBS for 10 min each and then incubated with secondary antibodies (Alexa Fluor-594 anti-rabbit, 1:200; Alexa Fluor-594 anti-rat, 1:200; and Alexa Fluor-633 anti-mouse, 1:200) for 2 h at room temperature. Coverslips were then washed four times with ice cold PBS for 10 min each, and mounted on glass slides using VECTASHIELD mounting medium with DAPI (Vector Laboratories). Images were acquired using a Zeiss LSM 880 confocal laser-scanning microscope. The staining was visualized in GFP-expressed neurons. Mean fluorescence intensity (MFI) was calculated over a specific region of interest, and background staining of the sections was measured and subtracted from the total signal to obtain the specific signal.

Hippocampal slices were collected 40 min after TBS and fixed in 4% PFA for 1 h and cryoprotected in 30% sucrose for 1 h at 4° C., and sectioned on a freezing microtome at 20 µm. Sections were blocked in 0.1 M PBS containing 5% goat serum and 0.3% Triton X-100, and then incubated in primary antibody mixture including chicken anti-GFP (1:500) and rabbit anti-p18 (1:200, Sigma) in 0.1 M PBS containing 1% BSA and 0.3% Triton X-100 overnight at 4° C. Sections were washed 3 times (10 min each) in PBS and incubated in Alexa Fluor 488 goat anti-chicken IgG and Alexa Fluor 594 goat anti-rabbit IgG for 2 h at room temperature. All images were taken in CA1 stratum radiatum between the stimulating and recording electrodes. The threshold for the GFP fluorescence was set to make sure that the control slices from naive mice or mice with AAV infection but without GFP reporter were considered GFP-negative.

For immunofluorescence with brain tissue section, deeply anesthetized animals were perfused and brains were post-fixed in 4% PFA overnight followed by sequential immersion in 15% and 30% sucrose for cryoprotection. Brains were then sectioned (20 µm) and stained as described above. The following primary antibodies were used: p18 (1:200, Sigma), LAMTOR4 (1:500, CST), RagA (1:100, CST), p14 (1:100, CST), MP1 (1:100, CST), RagB (1:100, CST)mTOR (1:100, CST), p-mTOR (1:100, CST), LAMP2 (1:200, Abcam), and PSD95 (1:200, Thermo). The hippocampal CA1 pyramidal cell soma and apical dendrites were randomly selected for colocalization analysis by Manders' coefficients. The apical dendrites in hippocampal CA1 stratum radiatum were also randomly selected for puncta analysis. The puncta number of p18/PSD95 was quantified and the percentage of p18 and PSD95 dually stained synapses was also analyzed.

Intrahippocampal AAV Injection. A dual convergent promoter system (U6 and H1 promoters) was employed where the sense and antisense strands of the siRNA are expressed by two different promoters rather than in a hairpin loop to avoid any possible recombination events. Stereotaxic AAV injection into CA1 region of the hippocampus was performed in 8-week-old mice. Animals were allocated into the experimental/control group in a randomized manner. Under isoflurane anesthesia, AAV p18 siRNA or AAV scrambled siRNA constructs in 2 µl solution were injected bilaterally into CA1 regions at two sites: 1.94 mm posterior to bregma, 1.4 mm lateral to the midline and 1.35 mm below the dura and 2.2 mm posterior to bregma, 1.8 mm lateral to the midline and 1.5 mm below the dura. The solution was slowly injected over 30 min and the needle was left in place for an additional 10 min. The needle was then slowly withdrawn and the incision closed. AAV-injected mice were used for experiments after four weeks, a period determined in pilot studies to be necessary for sufficient expression of viral mediated gene expression.

Image Analysis and Quantification. Images were acquired using a Nikon Cl or a Zeiss LSM 880 with Airyscan confocal laser-scanning microscope with a 60× objective. Images for all groups in a particular experiment were obtained using identical acquisition parameters and analyzed using ImageJ software (NIH). All immunostaining studies were performed in 3-5 independent experiments. In all cases the experimenter was blind regarding the identity of the transfected constructs and the genotypes during acquisition and analysis.

Dendritic Spine Analysis. Four weeks after AAV injection, mice were deeply anesthetized using gaseous isoflurane and then decapitated. The brain was rapidly removed and Golgi impregnation was performed according to our published protocol (Sun et al., 2016) and outlined in the FD Rapid GolgiStain Kit (FD Neurotechnologies, Ellicott, Md.). The number of spines located on randomly selected dendritic branches was counted manually by an investigator blind to genotype and injection. Spine density was calculated by dividing the number of spines on a segment by the length of the segment and was expressed as the number of spines per μm of dendrite. Spine types were determined on the basis of the ratio of the width of the spine head to the length of the spine neck and classified as previously described (Risher et al., 2015). Five to seven dendritic branches between 10 and 20 μm in length were analyzed and averaged to provide a section mean.

Fear Conditioning. AS mice and their WT littermates were randomly assigned to either control or p18 siRNA groups and blinded to the examiner. Four weeks after AAV injection, mice were placed in the fear-conditioning chamber (H10-11M-TC, Coulbourn Instruments). The conditioning chamber was cleaned with 10% ethanol to provide a background odor. A ventilation fan provided a background noise at ~55 dB. After a 2 min exploration period, three tone-footshock pairings separated by 1 min intervals were delivered. The 85 dB 2 kHz tone lasted 30 s and co-terminated with a footshock of 0.75 mA and 2 s. Mice remained in the training chamber for another 30 s before being returned to home cages. Context test was performed one day after training in the original conditioning chamber with 5 min recording. On day three, animals were subjected to cue/tone test in a modified chamber with different texture and color, odor, background noise, and lighting. After 5 min recording, mice was exposed to a tone (85 dB, 2 kHz) for 1 min. Mouse behavior was recorded with the Freezeframe software and data were analyzed using the Freezeview software (Coulbourn Instruments). Motionless bouts lasting more than 1 s were considered as freezing. The percent of time animal froze was calculated and group means with S.E.M. were analyzed.

Statistical Analysis. Error bars indicate standard error of the mean. To compute p values, unpaired Student's t test, and one- or two-way ANOVA with Tukey's post-test were used (GraphPad Prism 6), as indicated in figure legends. The level of statistical significance was set at p<0.05.

TABLE 1

Antibodies, chemicals, and plasmids used
Key Resources Table

| Reagent type (species) or resource | Designation | Source or reference | Identifiers | Additional information |
|---|---|---|---|---|
| strain, strain background (*Mus musculus*) | B6.129S7-Ube3a$^{tm1Alb}$/J | The Jackson Laboratory PMID: 9808466 | MGI: J:50811 | |
| strain, strain background | Control shRNA Lentiviral Particles | Santa Cruz Biotechnology | sc-108080 | |
| strain, strain background (*Mus musculus*) | P18 shRNA Lentiviral Particles | Santa Cruz Biotechnology | sc-108727-V | |
| strain, strain background | copGFP Control Lentiviral Particles | Santa Cruz Biotechnology | sc-108084 | |
| strain, strain background | Scrambled AAV9 siRNA Control Virus | Applied Biological Materials | iAAV01509 | |
| strain, strain background (*Mus musculus*) | P18 AAV9 siRNA Pooled Virus | Applied Biological Materials | iAAV04811709 | |
| strain, strain background | Scrambled AAV9 shRNA Control Virus | VectorBuilder | SP1001276 | Custom |
| strain, strain background (*Mus musculus*) | P18 AAV9 shRNA Virus | VectorBuilder | SP1001275 | Custom; target sequence: 5'-CGTATGCCTAT AGTGCACTTT-3' (SEQ ID NO: 1) |
| genetic reagent (*Homo sapiens*) | SMARTpool ON-TARGETplus Human UBE3A siRNA | Dharmacon | L-005137-00 | |
| genetic reagent | ON-TARGETplus Non-targeting Control Pool | Dharmacon | D-001810-10 | |
| genetic reagent (*Mus musculus*) | SMARTpool Accell Mouse Ube3a siRNA | Dharmacon | E-047237-00 | |
| genetic reagent | Accell Non-targeting Control Pool | Dharmacon | D-001910-10 | |

TABLE 1-continued

Antibodies, chemicals, and plasmids used
Key Resources Table

| Reagent type (species) or resource | Designation | Source or reference | Identifiers | Additional information |
|---|---|---|---|---|
| cell line (*Cercopithecus aethiops*) | COS-1 | ATCC | CRL-1650; RRID: CVCL_0223 | |
| antibody | anti-UBE3A (mouse monoclonal) | Sigma-Aldrich | E8655; RRID: AB_261956 | (1:2000) |
| antibody | anti-p18 (rabbit monoclonal) | Cell Signaling Technology | 8975; RRID: AB_10860252 | (1:1000) |
| antibody | anti-p18 (rabbit polyclonal) | Sigma-Aldrich | HPA002997; RRID: AB_1845531 | (1:200) |
| antibody | anti-p14 (rabbit monoclonal) | Cell Signaling Technology | 8145; RRID: AB_10971636 | (1:1000) |
| antibody | anti-MP1 (rabbit monoclonal) | Cell Signaling Technology | 8168; RRID: AB_10949501 | (1:1000) |
| antibody | anti-LAMTOR4 (rabbit monoclonal) | Cell Signaling Technology | 12284 | (1:500) |
| antibody | anti-RagA (rabbit monoclonal) | Cell Signaling Technology | 4357; RRID: AB_10545136 | (1:1000) |
| antibody | anti-RagB (rabbit monoclonal) | Cell Signaling Technology | 8150; RRID: AB_11178806 | (1:1000) |
| antibody | anti-RagC (rabbit monoclonal) | Cell Signaling Technology | 5466; RRID: AB_10692651 | (1:1000) |
| antibody | anti-ubiquitin (mouse monoclonal) | Enzo Life Sciences | BML-PW8810; RRID: AB_10541840 | (1:800) |
| antibody | anti-Flag (mouse monoclonal) | Sigma-Aldrich | F1804; RRID: AB_262044 | (1:1000) |
| antibody | anti-LAMP2 (rat monoclonal) | Abcam | ab13524; RRID: AB_2134736 | (1:200) |
| antibody | anti-LAMP1 (mouse monoclonal) | Abcam | ab25630; RRID: AB_470708 | (1:20) |
| antibody | anti-p-mTOR Ser2448 (rabbit polyclonal) | Cell Signaling Technology | 2971; RRID: AB_330970 | (1:1000) |
| antibody | anti-mTOR (rabbit polyclonal) | Cell Signaling Technology | 2972; RRID: AB_330978 | (1:1000) |
| antibody | anti-p-S6K1 Thr389 (rabbit polyclonal) | Cell Signaling Technology | 9205; RRID: AB_330944 | (1:1000) |
| antibody | anti-S6K1 (rabbit polyclonal) | Cell Signaling Technology | 9202; RRID: AB_331676 | (1:1000) |
| antibody | anti-p-S6 Ser240/244 (rabbit polyclonal) | Cell Signaling Technology | 2215; RRID: AB_331682 | (1:1000) |
| antibody | anti-S6 (rabbit monoclonal) | Cell Signaling Technology | 2217; RRID: AB_331355 | (1:1000) |
| antibody | anti-p-PKC (rabbit polyclonal) | Cell Signaling Technology | 9371; RRID: AB_2168219 | (1:1000) |
| antibody | anti-PKCα (rabbit polyclonal) | Cell Signaling Technology | 2056; RRID: AB_2284227 | (1:1000) |
| antibody | anti-p-4EBP1 Ser65 (rabbit polyclonal) | Cell Signaling Technology | 9451; RRID: AB_330947 | (1:1000) |
| antibody | anti-4EBP1 (rabbit monoclonal) | Cell Signaling Technology | 9644; RRID: AB_2097841 | (1:1000) |

TABLE 1-continued

Antibodies, chemicals, and plasmids used
Key Resources Table

| Reagent type (species) or resource | Designation | Source or reference | Identifiers | Additional information |
|---|---|---|---|---|
| antibody | anti-p-AKT Ser473 (rabbit monoclonal) | Cell Signaling Technology | 4060; RRID: AB_2315049 | (1:1000) |
| antibody | anti-AKT (rabbit polyclonal) | Cell Signaling Technology | 9272; RRID: AB_329827 | (1:1000) |
| antibody | anti-Raptor (mouse monoclonal) | EMD Millipore | 05-1470; RRID: AB_10615925 | (1:500) |
| antibody | anti-Rictor (rabbit polyclonal) | Bethyl Laboratories | A300-459A; RRID: AB_2179967 | (1:200) |
| antibody | anti-NeuN (mouse monoclonal) | EMD Millipore | MAB377; RRID: AB_2298772 | (1:100) |
| antibody | anti-PSD95 (mouse monoclonal) | Thermo Fisher Scientific | MA1-045; RRID: AB_325399 | (1:200) |
| antibody | anti-Cathepsin B (mouse monoclonal) | EMD Millipore | IM27L; RRID: AB_2274848 | (1:400) |
| antibody | anti-COXIV (rabbit monoclonal) | Cell Signaling Technology | 4850; RRID: AB_2085424 | (1:1000) |
| antibody | anti-GFP (chicken polyclonal) | Thermo Fisher Scientific | A10262; RRID: AB_2534023 | (1:500) |
| antibody | anti-GAPDH (mouse monoclonal) | EMD Millipore | MAB374; RRID: AB_2107445 | (1:1000) |
| antibody | anti-β-actin (mouse monoclonal) | Sigma-Aldrich | A5441; RRID: AB_476744 | (1:10,000) |
| antibody | Goat anti-rabbit IgG IRDye® 680RD | LI-COR Biosciences | 926-68071 | (1:10,000) |
| antibody | Goat anti-mouse IgG IRDye® 800CW | LI-COR Biosciences | 926-32210 | (1:10,000) |
| antibody | Alexa 488-secondaries | Molecular Probes | | (1:400) |
| antibody | Alexa 594- or 633-secondaries | Molecular Probes | | (1:200) |
| recombinant DNA reagent | HA-tagged wild-type Ube3a | Addgene PMID: 9497376 | 8648 | |
| recombinant DNA reagent | HA-tagged Ube3a-C833A | Addgene PMID: 9497376 | 8649 | |
| recombinant DNA reagent | HA-p18 | Addgene PMID: 22980980 | 42338 | |
| recombinant DNA reagent | HA-p18G2A | Addgene PMID: 22980980 | 42327 | |
| recombinant DNA reagent | Flag-p18 | Addgene PMID: 22980980 | 42331 | |
| recombinant DNA reagent | Flag-p18ΔK | This paper | N/A | Custom Gene Synthesis from Integrated DNA Technologies (all lysine residues in p18 mutated into arginine) |
| recombinant DNA reagent | Flag-p18K20R | This paper | N/A | Site-directed mutagenesis using a QuikChange II site-directed mutagenesis kit (Agilent). The mutation was confirmed by sequencing. |

TABLE 1-continued

Antibodies, chemicals, and plasmids used
Key Resources Table

| Reagent type (species) or resource | Designation | Source or reference | Identifiers | Additional information |
|---|---|---|---|---|
| recombinant DNA reagent | Flag-p18K31R | This paper | N/A | Same as above |
| recombinant DNA reagent | Flag-p18K60R | This paper | N/A | Same as above |
| recombinant DNA reagent | Flag-P18K103/104R | This paper | N/A | Same as above |
| recombinant DNA reagent | Flag-p18K151R | This paper | N/A | Same as above |
| recombinant DNA reagent | His-ubiquitin | Addgene PMID: 21183682 | 31815 | |
| peptide, recombinant protein | Recombinant human p18 | CUSABIO | CSB-EP757561XBF | |
| commercial assay or kit | E6AP (UBE3A) Ubiquitin Ligase Kit | Boston Biochem | K-240 | |
| commercial assay or kit | FD Rapid GolgiStain Kit | FD Neurotechnologies | PK401 | |
| chemical compound, drug | MG132 | EMD Millipore | 474790 | 10 μM |
| chemical compound, drug | Bafilomycin A1 | Sigma-Aldrich | B1793 | 100 nM |
| chemical compound, drug | MHY1485 | EMD Millipore | 500554 | 2 μM |
| chemical compound, drug | Rhodamine Phalloidin | Molecular Probes | R415 | |
| software, algorithm | ImageJ | https://imagej.nih.gov/ij/ | RRID: SCR_003070 | |
| software, algorithm | Prism 6 | GraphPad Software | RRID: SCR_002798 | |

Figure 9:
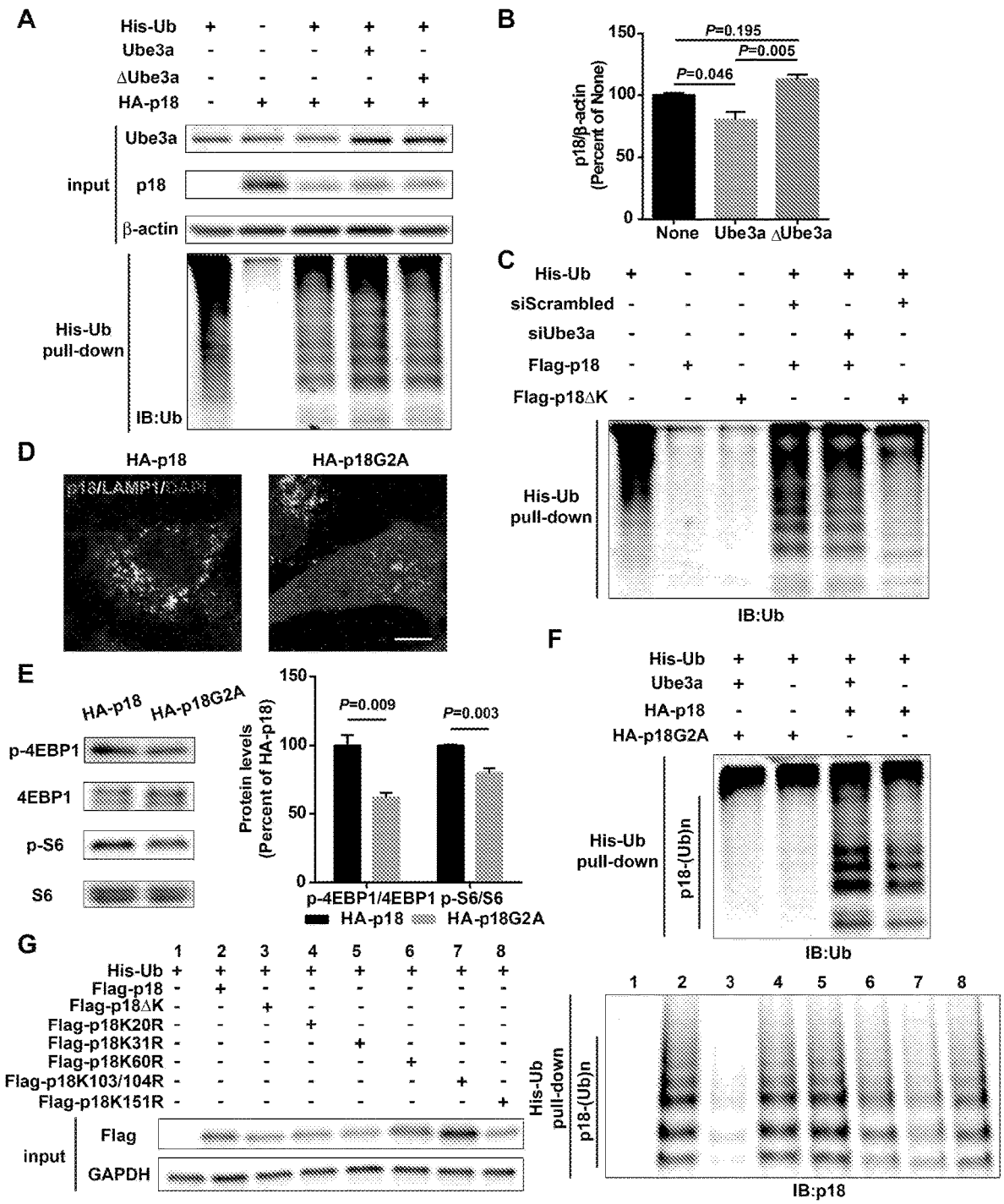
FIG. 9(A-F) shows His-ubiquitin pull down analyses of p18 ubiquitination. (A)His-ubiquitin pull down assay performed following overexpression of Ube3a or ΔUbe3a. Upper panel: Levels of input proteins were evaluated by Western blot probed with Ube3a, p18, and β-actin antibodies. Lower panel: Levels of ubiquitin were determined by Western blot analysis. This image is paired with FIG. 1E. (B) Quantitative analysis of blots in FIG. 1F (means±SEM, p=0.046 None vs Ube3a, p=0.005 Ube3a vs ΔUbe3a, p=0.195 None vs ΔUbe3a, n=3 independent experiments, one-way ANOVA with Tukey's post hoc analysis). (C)His-ubiquitin pull down assay performed following Ube3a siRNA treatment. Levels of ubiquitin were determined by Western blot analysis. This image is paired with FIG. 1G. (D) Localization of wild-type p18 and p18G2A proteins. COS-1 cells expressing p18 or p18G2A were stained with anti-p18 antibody (red) and anti-LAMP1 antibody (green). Scale bar=10 μm. (E) Western blot analysis using anti-p-4EBP1, 4EBP1, p-S6, or S6 antibodies of lysates from COS-1 cells transfected with HA-p18 or HA-p18G2A. Right, quantitative analysis of blots. N=3 independent experiments, p=0.009 for p-4EBP1, and p=0.003 for p-S6 (unpaired, two-tailed Student's t test). (F) His-ubiquitin pull down assay performed using HA-p18 or HA-p18G2A. Levels of ubiquitin were determined by Western blot analysis. This image is paired with FIG. 1H.

Example 1: P18 is a Ube3a substrate. Although it has been shown that p18 plays essential roles in mTOR and MAP kinase signaling and other cellular functions, very little is known regarding its biosynthesis and degradation. It was first determined whether Ube3a could regulate p18 levels in heterologous cells. Western blot analysis showed that Ube3a knockdown (KD) in COS-1 cells by siRNA resulted in increased p18 levels, as compared to scrambled control siRNA (FIG. 1A). Sequence analysis revealed the presence of 6 lysine residues in p18, which could represent ubiquitination sites (FIG. 1B). To assess whether p18 could be a Ube3a substrate, it was first determined whether these 2 proteins exhibited direct interactions. Co-immunoprecipitation experiments using extracts from COS-1 cells transfected with Ube3a and Flag-p18 showed that p18 could bind to Ube3a in an E3 ligase activity-independent manner, since p18 could also bind to an inactive form of Ube3a with a mutation in its catalytic site, Ube3a-C833A (Kumar et al., 1999) (referred to as ΔUbe3a hereafter) (FIG. 1C). In vitro ubiquitination assays using purified recombinant p18 and a Ube3a ubiquitination assay kit showed that p18 ubiquitination was only observed in the presence of Ube3a, ubiquitin, E1, E2, and ATP (FIG. 1D). Whether Ube3a could ubiquitinate p18 in intact cells was then determined using His-ubiquitin pull-down assay. COS-1 cells were co-transfected with p18 and His-ubiquitin plus either an empty vector, or Ube3a or ΔUbe3a. Ubiquitinated proteins were extracted by Co-affinity chromatography and analyzed by Western blot. Co-transfection with Ube3a, but not ΔUbe3a, resulted in massive p18 ubiquitination (FIG. 1E and FIG. 9A). In addition, transfection with Ube3a, but not ΔUbe3a, resulted in decreased p18 levels (FIG. 1F and FIG. 9B), indicating that Ube3a-mediated regulation of p18 levels depends on its E3 ligase activity and p18 ubiquitination. Finally, to confirm that Ube3a-mediated p18 ubiquitination was taking place on lysine residues, all lysine residues were simultaneously mutated into arginine (AK) in Flag-p18. COS-1 cells were first transfected with either Ube3a siRNA or a scrambled control siRNA, followed by transfection with Flag-p18 or Flag-p18ΔK and His-ubiquitin. His-ubiquitin pull-down assay showed that levels of p18-immunopositive high molecular weight bands, i.e., ubiquitinated p18, were significantly reduced following Ube3a siRNA KD (FIG. 1G and FIG. 9C), and the degree of reduction (100.0±1.8 vs. 66.8±3.7, n=4, p<0.001) corresponded to the extent of Ube3a down-regulation (100.0±2.4 vs. 60.9±5.2, n=4, p<0.001). Furthermore, p18 ubiquitination was abolished by K-R mutations (FIG. 1G and FIG. 9C). ΔK mutations did not significantly affect the interaction between p18 and Ube3a (FIG. 1C). These results confirmed that p18 is ubiquitinated by Ube3a at lysine residues.

Previous studies have revealed that p18 is anchored to lysosomal membranes through myristate and palmitate modifications at G2 and C3/C4, respectively (Nada et al., 2014). It was confirmed that wild-type (WT) p18 was indeed localized at the lysosomal surface, while its myristoylation-defective mutant, p18G2A, failed to localize to the lysosomal surface and partially (due to the existence of endogenous p18) blocked mTORC1 activation (FIGS. 9D-E), and nearly completely lost its ability to be ubiquitinated (FIG.

1H and FIG. 9F). These results suggest that myristoylation-dependent lysosomal localization of p18 is critical for both mTORC1 activation and Ube3a-mediated p18 ubiquitination.

Table 2 shows different methods of reducing p18 expression with different inhibitory RNA approaches.

TABLE 2

|  | Target Sequences | Knockdown Effect |
|---|---|---|
| AAV shRNA (mouse) | CGTATGCCTATAGTGCACTTT (SEQ ID NO: 1) | Tested; Good |
|  | GCGAAAGAAGAGCTGGTTGTA (SEQ ID NO: 2) | Tested; Not as good as the above one |
|  | CCTGCTACTAATCACGGAGAA (SEQ ID NO: 3) | Not tested because the knockdown score is not high |
|  | CCAACTACCATAGCCTACCTT (SEQ ID NO: 4) | Not tested because the knockdown score is not high |
|  | GCTGGTTGTACAGTTTGGGAT (SEQ ID NO: 5) | Not tested because the knockdown score is not high |
|  | GCCCTGCTTTCCTCCATCCTT (SEQ ID NO: 6) | Not tested because the knockdown score is not high |
| AAV siRNA (mouse) | AGCCCAACTACCATAGCCTACCTTCAGCT (SEQ ID NO: 7) | Tested; Good; Pooled Virus |
|  | TCCCAGGGCATGGAACAGCATGAGTACAT (SEQ ID NO: 8) |  |
|  | TGGAAGAAGCTGCCACCGTTGCCATCTCT (SEQ ID NO: 9) |  |
|  | CGCGTGGATGCGAAAGAAGAGCTGGTTGT (SEQ ID NO: 10) |  |
| Lentivirus siRNA (mouse) | GCATGGAACAGCATGAGTA (SEQ ID NO: 11) | Tested; Good; Pooled Virus |
|  | GTACCTAACCTGCTACTAA (SEQ ID NO: 12) |  |
| Accell siRNA (mouse) | GCTTGAGTCTGAATTGAGT (SEQ ID NO: 13) | Tested; Good; SMARTpool |
|  | CCTCGATAAAGAAAGTATA (SEQ ID NO: 14) |  |
|  | GCGTGGATGCGAAAGAAGA (SEQ ID NO: 15) |  |
|  | TGCGTATGCCTATAGTGCA (SEQ ID NO: 16) |  |
| CRISPR/Cas9 sgRNA (human) | TCCGCTCGCACTGATGAGCA (SEQ ID NO: 17) | Tested; Good |
|  | GATCCGTGTGGACGCAAAAG (SEQ ID NO: 18) | Tested; Not as good as the above one |

Knockdown scores were determined using VectorBuilder® software. VectorBuilder applies rules similar to that used by the RNAi consortium (TRC) to design and score shRNAs. In using the CRISPR/Cas9 system to knockout p18, sequence encoding the sgRNA was introduced into a CRISPR pX330 plasmid using standard protocols. See Cong et al.

Figure 2:
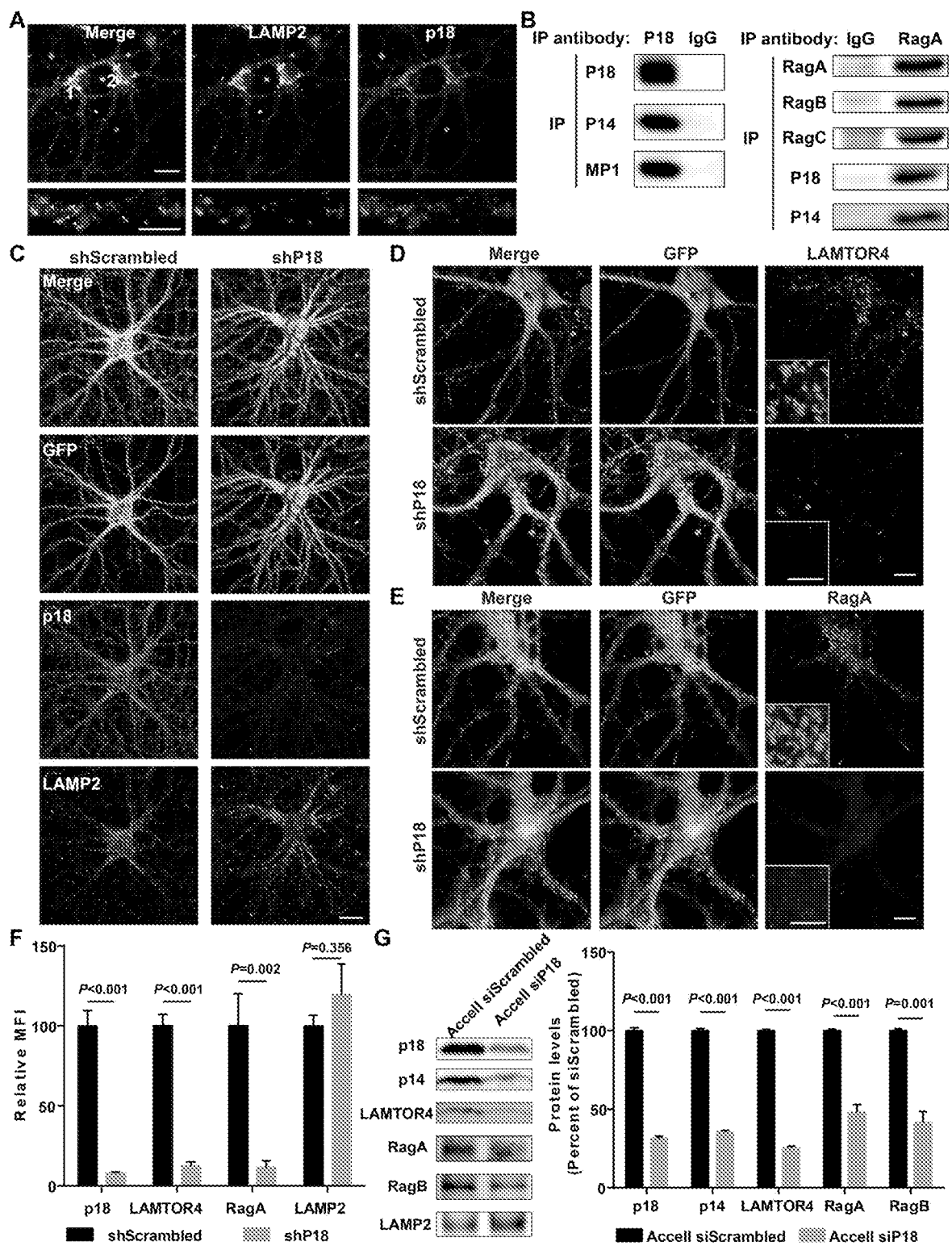
FIG. 2(A-G) shows characterization of p18 in hippocampal neurons. Images of cultured hippocampal neurons co-immunostained for lysosomal protein LAMP2 (green) and p18 (red). Insets are enlarged images of LAMP2- and p18-immunoreactive puncta along the dendrites. Arrowheads indicate co-localized puncta. Scale bar: top, 20 µm; inset, 10 µm. Left, p18 forms complex with p14 and MP1 in hippocampal neurons. Lysates from cultured hippocampal neurons were immunoprecipitated with an anti-p18 antibody or control IgG and probed with the indicated antibodies. Right, RagA co-immunoprecipitates RagB, RagC, p18, and p14. Lysates from mouse hippocampi were immunoprecipitated with an anti-RagA antibody or control IgG and probed with the indicated antibodies. (C) Images of cultured hippocampal neurons co-immunostained for p18 (magenta) and LAMP2 (red). Neurons were infected with shRNA AAV directed against p18 with GFP co-expression or scrambled shRNA control before processing for immunofluorescence assay and imaging. Scale bar, 20 µm. (D) Images of hippocampal neurons stained for LAMTOR4 (red). Cells were infected and processed as in (C). Scale bar, 10 µm; inset, 5 µm. (E) Images of hippocampal neurons stained for RagA (red). Cells were infected and processed as in (C). Scale bar, 10 µm; inset, 5 µm. (F) Quantification of fluorescent signals for p18 (n=13, p<0.001), LAMTOR4 (n=11, p<0.001), RagA (n=6, p=0.002), and LAMP2 (n=6, p=0.356) in control shRNA and p18 shRNA-infected neurons shown in C-E. Student's t test. Note that n refers to the number of culture dishes analyzed. (G) Left, Western blot analysis of p18, p14, LAMTOR4, RagA, RagB, and LAMP2 in enriched lysosomal fractions prepared from WT neurons transfected with Accell control or p18 siRNA. Right, quantitative analysis of blots. Results are expressed as % of values in control siRNA-transfected WT neurons and shown as means±S.E.M. N=3 independent experiments, p<0.001 for p18, p14, LAMTOR4, and RagA, p=0.001 for RagB (unpaired, two-tailed Student's t test). See also FIG. 10.
Figure 10:
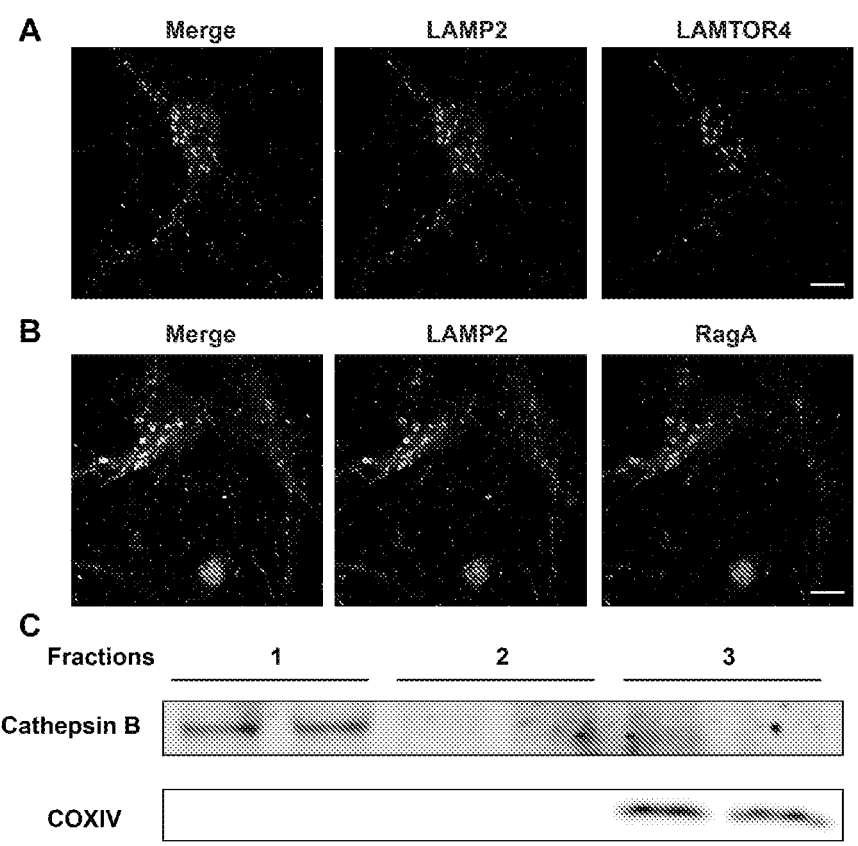
FIG. 10(A-C) shows localization of LAMTOR4 and RagA in hippocampal neurons, and representation of organelle marker proteins in individual OptiPrep™ fractions. (A) Images of cultured hippocampal neurons co-immunostained for lysosomal protein LAMP2 (green) and LAMTOR4 (red). Scale bar=10 µm. (B) Images of hippocampal neurons co-immunostained for lysosomal protein LAMP2 (green) and RagA (red). Scale bar=10 µm. (C) Three individual fractions collected after density gradient centrifugation of cultured neurons were assessed using antibodies against Cathepsin B (lysosomes) and COXIV (mitochondria).

Example 2. P18 is essential for lysosomal localization of Ragulator and RagGTPases in hippocampal neurons. Since there is little information regarding p18 in the CNS, p18 expression in hippocampal neurons was characterized. Double immunolabeling with antibodies against p18 and LAMP2, a well-characterized lysosomal marker (Eskelinen, 2006), showed that p18 was co-localized with LAMP2, not only in cell bodies but also in dendrites of cultured mouse hippocampal neurons (FIG. 2A). To test whether p18 could interact with other members of the Ragulator complex in neurons as in other cell types, neuronal lysates were immunoprecipitated from cultured hippocampal neurons with a p18 antibody and the precipitated material was probed with anti-p18, anti-p14, or anti-MP1 antibodies. p18, p14, and MP1 were detected in anti-p18—but not in control IgG-pull-down proteins (FIG. 2B). Immunoprecipitates prepared from hippocampal lysates of WT mice with a RagA antibody, but not a control IgG, consistently contained RagA, RagB, RagC, p18, and p14 (FIG. 2B). These results indicate that p18 interacts with other members of the Ragulator complex and that the Ragulator interacts with Rag GTPases in hippocampal neurons, as in other cell types. To further investigate whether p18 also serves as an anchor for the Ragulator-Rag complex in the brain, neurons were infected with shRNA AAV directed against p18 to decrease p18 expression and with GFP co-expression to visualize infected neurons, and the effects on the Ragulator-Rag complex were determined. Confocal images of infected neurons indicated that p18 shRNA infection efficiently reduced p18 expression in cultured neurons, while lysosomal morphology was not obviously affected (FIGS. 2C and F). Notably, levels of lysosome-localized LAMTOR4 and RagA (FIG. 10(A-B)) were significantly reduced following p18 shRNA KD in neurons (FIG. 2D-F). Lysosomal fractions were also prepared from neuronal cultures treated with Accell control or p18 siRNA to determine the levels of members of the Ragulator-Rag complex. Western blot analysis demonstrated that the lysosomal fraction was enriched with the lysosomal protease cathepsin B, but did not contain the mitochondrial marker COXIV (FIG. 10C). Consistent with the immunofluorescence results, lysosomal levels of p18, p14, LAMTOR4, as well as RagA and RagB were significantly reduced by p18 KD (FIG. 2G). Thus, p18 is required for lysosomal targeting of the Ragulator-Rag complex in neurons.

Figure 3:
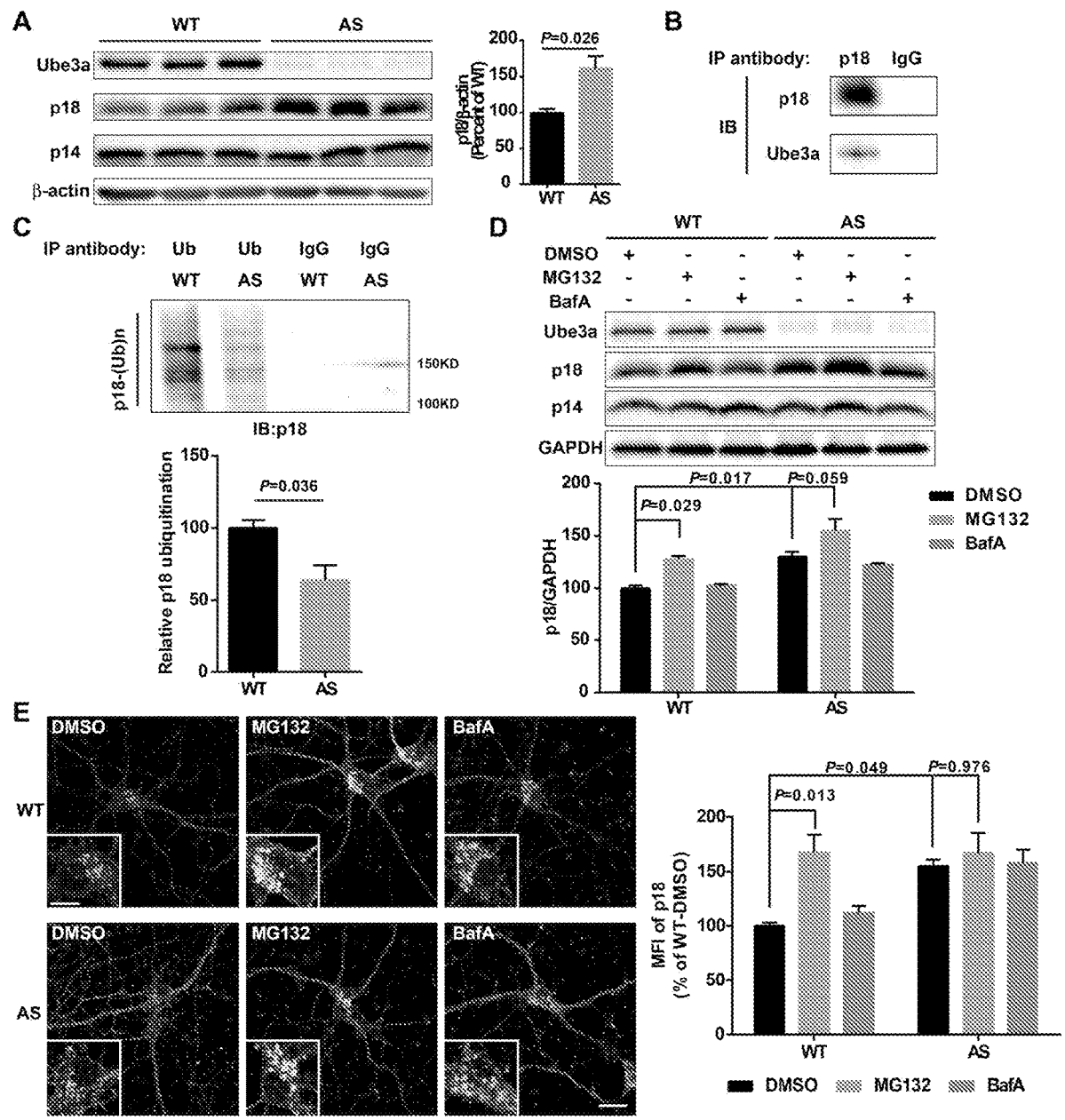
FIG. 3(A-E) shows that Ube3a regulates p18 levels in a proteasome-dependent manner in hippocampal neurons. (A) Left, Western blot analysis of p18 and p14 levels in crude membrane fractions (P2) of hippocampi from WT and AS mice. Right, quantitative analysis of blots. Results are expressed as % of values in WT mice and shown as means±S.E.M. N=3 mice, p=0.026 (unpaired, two-tailed Student's t test). (B) Interactions between Ube3a and p18 in hippocampal neuron cultures. Western blot analysis with anti-p18 and -Ube3a antibodies of immunoprecipitation performed with anti-p18 antibodies or control IgG. (C) Immunoprecipitation of hippocampal P2 fractions from WT and AS mice under denaturing conditions was performed with anti-ubiquitin antibodies or control IgG and Western blots were labelled with anti-p18 antibodies. Ubiquitinated p18 proteins are indicated as "p18-(Ub)n". Lower panel: quantification of the relative abundance of ubiquitinated p18 in hippocampus of WT and AS mice (mean±SEM, p=0.036 compared to WT mice, n=3 mice, Student's t test). (D) Effects of acute MG132 or Bafilomycin A1 (BafA) treatment on p18 and p14 levels in hippocampus slices of WT and AS mice. Upper panel: representative Western blot images; lower panel: quantitative analysis of blots in upper panel. N=3 independent experiments, p=0.029 WT/DMSO vs WT/MG132, p=0.017 WT/DMSO vs AS/DMSO, p=0.059 AS/DMSO vs AS/MG132, two-way ANOVA with Tukey's post-test. (E) Representative images of p18 in WT and AS hippocampal neurons treated with DMSO, MG132, and BafA; insets: enlarged cell bodies. Right: Quantitative analysis of images. Data are expressed as mean±SEM. N=3 independent experiments, p=0.013 WT/DMSO vs WT/MG132, p=0.049 WT/DMSO vs AS/DMSO, p=0.976 AS/DMSO vs AS/MG132; two-way ANOVA with Tukey's post hoc analysis. Scale bar=20 µm and 10 µm in insets. See also FIG. 11.
Figure 11:
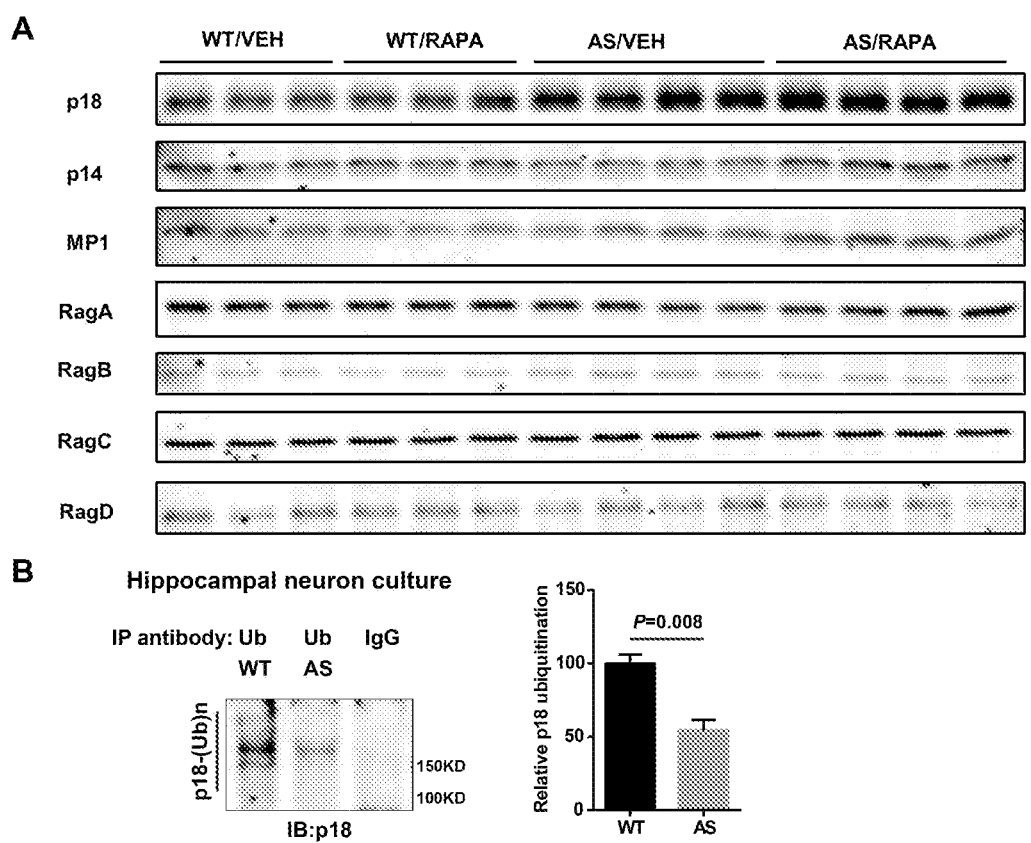
FIG. 11(A-B) shows levels of members of the Ragulator-Rag complex in WT and AS mice and in vivo denaturing immunoprecipitation assay of p18 ubiquitination. (A) Representative images of Western blots labeled with p18, p14, MP1, RagA, RagB, RagC, and RagD in P2 fractions of hippocampus from vehicle (VEH)- and rapamycin (RAPA)-treated WT and AS mice. (B) Immunoprecipitation of lysates from WT and AS hippocampal neuron cultures under denaturing conditions was performed with anti-ubiquitin antibodies or control IgG and Western blots were labelled with anti-p18 antibodies. Ubiquitinated p18 proteins are indicated as "p18-(Ub)n". Right panel: quantification of the relative abundance of ubiquitinated p18 (mean±SEM, p=0.008, n=3 independent experiments, Student's t test). (C) Levels of input proteins were evaluated by Western blot probed with Ube3a and p18 antibodies. This image is paired with FIG. 3C.

Example 3. Ube3a regulates p18 levels in a proteasome-dependent manner in hippocampal neurons. It was then determined whether Ube3a deficiency in neurons could result in increased p18 levels using AS mice. Western blot results showed that p18 levels were markedly increased in crude membrane fractions (P2) of hippocampus from AS mice, as compared to WT mice (FIG. 3A and FIG. 11A), while there was no significant change in levels of p14, MP1, as well as Rag GTPases (FIG. 3A and FIG. 11A). Importantly, although rapamycin treatment of AS mice normalized mTORC1 and mTORC2 signaling (Sun et al., 2016), it did not reverse the increase in p18 levels in AS mice (FIG. 11A, same samples as those used in Sun et al., 2016). These results suggest that increased p18 levels in AS mice are independent of mTORC1 activity, and that increased mTORC1 activity might be downstream of p18 level increases.

The data suggested that increased p18 levels in hippocampus of AS mice could be due to the lack of Ube3a-mediated p18 ubiquitination and subsequent degradation. To confirm this possibility, it was first shown that p18 was co-immunoprecipitated with Ube3a in cultured hippocampal neurons from WT mice (FIG. 3B). Ubiquitinated proteins from cultured hippocampal neurons or P2 fractions of hippocampi from WT and AS mice were immunoprecipitated with ubiquitin antibodies under denaturing conditions, and precipitated proteins were processed for Western blot with ubiquitin and p18 antibodies. Both p18 and ubiquitin antibodies labeled high molecular weight bands, and the intensity of p18-immunopositive bands was much weaker in samples from AS mice than WT mice (FIG. 3C and FIG. 11(B-C)), indicating that the increase in p18 levels in AS mice is likely due to a deficit in Ube3a-mediated p18 ubiquitination and degradation.

To determine whether Ube3a-mediated regulation of p18 was proteasome- and/or lysosome-dependent, acute hippocampal slices from WT and AS mice were treated with either a proteasome inhibitor, MG132 (10 μM), or a lysosome inhibitor, the vacuolar H+-ATPase (V-ATPase) inhibitor, bafilomycin A1 (BafA, 100 nM), for 30 min. These concentration and treatment duration have previously been shown to significantly inhibit proteasome or lysosomal function, respectively (Kim et al., 2015). As expected, levels of p18 were significantly higher in vehicle-treated slices from AS mice than in vehicle-treated slices from WT mice. Incubation of hippocampal slices with MG132, but not BafA, significantly increased p18 levels in WT slices and marginally in AS slices, possibly due to the residual expression of paternal Ube3a (FIG. 3D). In addition, MG132 treatment (10 μM, 4 h) markedly increased p18 intensity in cultured hippocampal neurons from WT mice, while BafA treatment (100 nM, 4 h) only slightly increased p18 in cultured hippocampal neurons from both WT and AS mice (FIG. 3E). These results strongly suggest that Ube3a decreases p18 levels via ubiquitination followed by proteasomal degradation.

Figure 4:
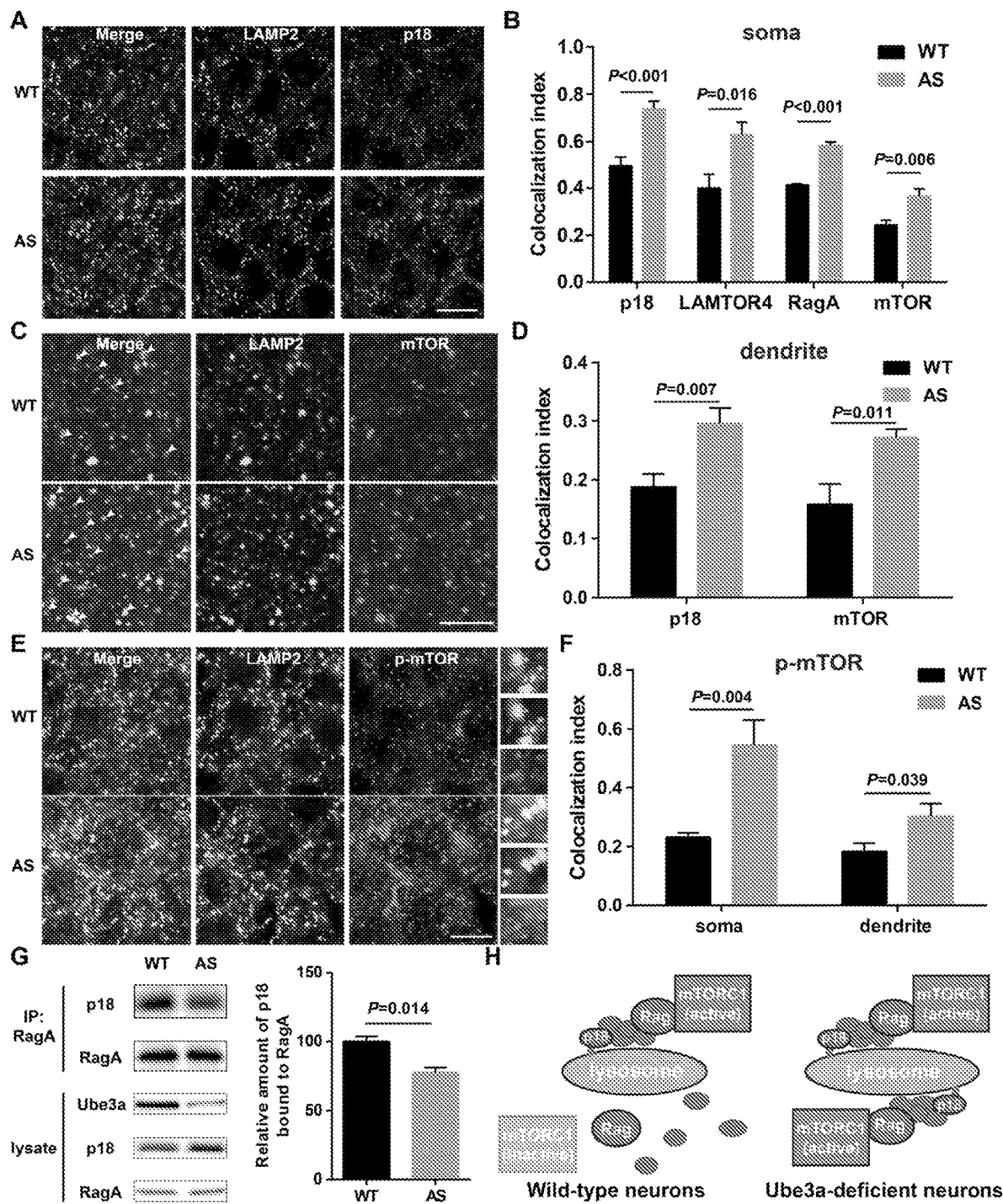
FIG. 4(A-H) shows Lysosomal localization of Ragulator-Rag complex and mTOR/p-mTOR in WT and AS mice. (A) Co-localization of p18 (red) with LAMP2 (green) in cell bodies of CA1 pyramidal neurons from WT and AS mice. Scale bar=10 µm. (B) Quantification of p18-LAMP2 (n=8 mice, p<0.001), LAMTOR4-LAMP2 (n=6 mice, p=0.016), RagA-LAMP2 (n=6 mice, p<0.001), and mTOR-LAMP2 (n=8 mice, p=0.006) colocalization in cell bodies of CA1 pyramidal neurons from WT and AS mice shown in A and FIG. 12(A-C). Unpaired t-test. (C) Representative images of apical dendrites of CA1 pyramidal neurons stained with anti-mTOR (red) and -LAM P2 (green) antibodies. Arrowheads indicate puncta with dual staining. Scale bar=5 µm. (D) Quantification of p18-LAMP2 (n=8 mice, p=0.007) and mTOR-LAMP2 (n=7 mice, p=0.011) co-localization in apical dendrites of CA1 pyramidal neurons from WT and AS mice. Unpaired t-test. (E) Co-localization of p-mTOR (red) with LAMP2 (green) in cell bodies of CA1 pyramidal neurons from WT and AS mice. Scale bar=10 µm. Insets show selected fields that were magnified ten times. (F) Quantification of p-mTOR-LAMP2 co-localization in cell bodies (p=0.004) and dendrites (p=0.039) of CA1 pyramidal neurons from WT and AS mice. N=6 mice, unpaired t-test. (G) Homogenates from WT and AS mouse hippocampus were immunoprecipitated with an anti-RagA antibody and probed with the indicated antibodies. Right, quantification of the relative abundance of p18 bound to RagA (mean±SEM, p=0.014, n=3 mice, Student's t test). (H) Model proposing that the Ragulator interacts with Rag, which in turn recruits mTORC1 to be activated on lysosomes in neurons. In Ube3a-deficient neurons, increased Ragulator-Rag complex on lysosomes results in mTORC1 over-activation. See also FIG. 12 and FIG. 13.
Figure 12:
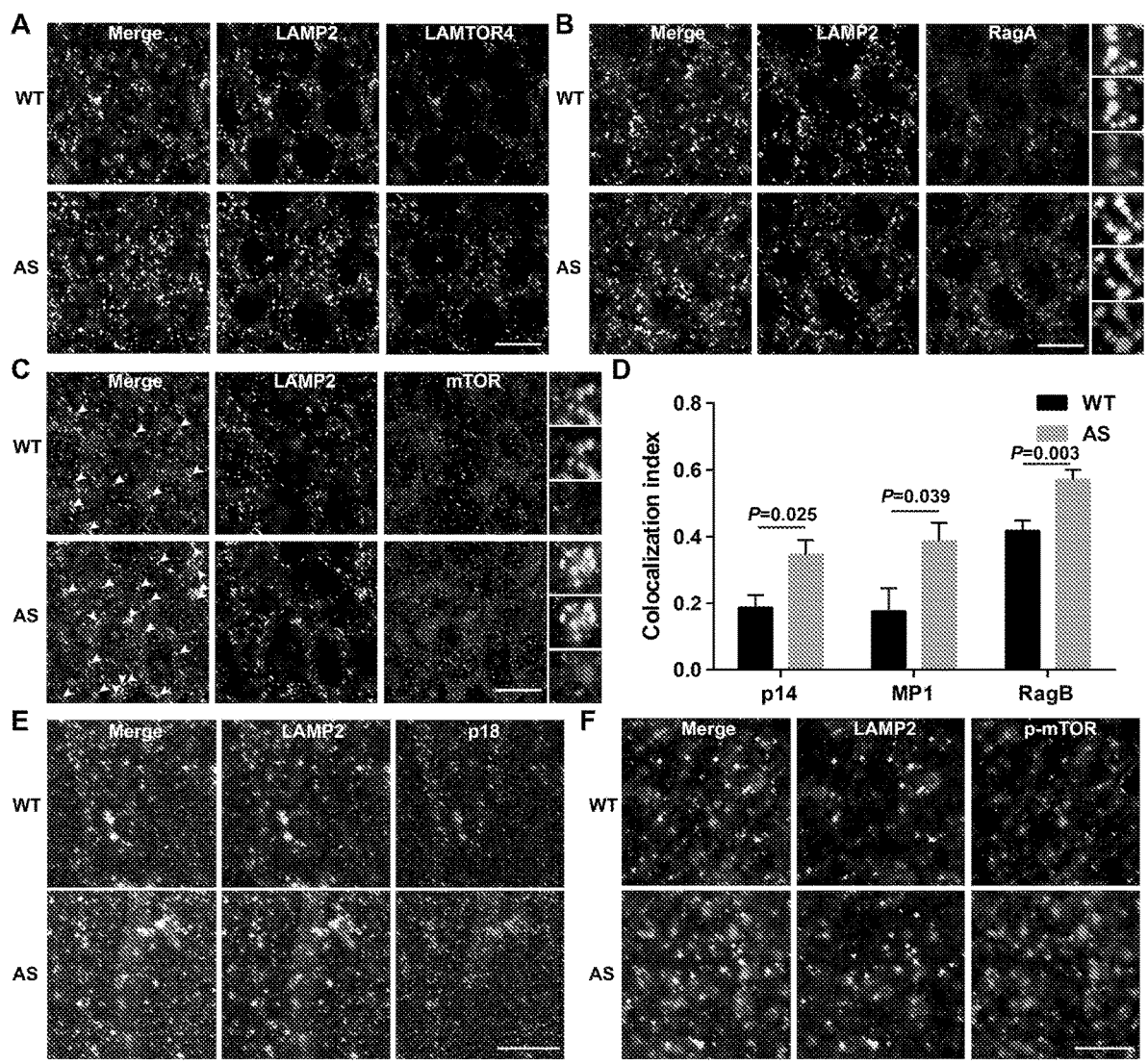
FIG. 12(A-F) shows lysosomal localization of members of the Ragulator-Rag complex and mTOR/p-mTOR in hippocampus of WT and AS mice. (A) Co-localization of LAMTOR4 (red) with LAMP2 (green) in cell bodies of CA1 pyramidal neurons from WT and AS mice. Scale bar=10 µm. (B) Co-localization of RagA (red) with LAMP2 (green) in cell bodies of CA1 pyramidal neurons from WT and AS mice. Scale bar=10 µm. (C) Co-localization of mTOR (red) with LAMP2 (green) in cell bodies of CA1 pyramidal neurons from WT and AS mice. Arrowheads indicate co-localized puncta. Scale bar=10 µm. In B and C, insets show selected fields that were magnified ten times. (D) Quantification of p14-LAMP2 (n=5 mice, p=0.025), MP1-LAMP2 (n=6 mice, p=0.039), and RagB-LAMP2 (n=11 WT mice, and 9 AS mice, p=0.003) colocalization in cell bodies of CA1 pyramidal neurons from WT and AS mice. Unpaired t-test. (E) Representative images of apical dendrites of CA1 pyramidal neurons stained with anti-p18 (red) and -LAMP2 (green) antibodies. Scale bar=10 µm. (F) Representative images of apical dendrites of CA1 pyramidal neurons stained with anti-p-mTOR (red) and -LAMP2 (green) antibodies. Scale bar=5 µm.

Example 4. Increased p18 levels in AS mice are associated with increased lysosomal localization of the Ragulator-Rag complex and mTOR. Immunofluorescent staining showed that p18 was clearly co-localized with LAMP2 in CA1 pyramidal neurons (NeuN/LAMP2 double stain shown in FIG. 13A), especially in cell bodies, in both WT and AS mice, and that more p18/LAMP2 double-stained puncta were detected in AS than in WT mice (FIGS. 4A-B). Similarly, lysosomal localization of other members of the Ragulator, LAMTOR4 (FIG. 4B and FIG. 12A), p14 and MP1 (FIG. 12D) was also increased in CA1 pyramidal cell soma of AS, as compared to WT mice. Furthermore, dual immunohistochemical staining for either RagA/B or mTOR with LAMP2 showed that co-localization of these proteins with LAMP2 was markedly increased in AS mice, as compared to WT mice (FIG. 4B and FIG. 12(B-D)). p18 was also clearly co-localized with LAMP2 in apical dendrites in hippocampal CA1 region of adult mice, and more p18/LAMP2 double-stained puncta were detected in AS than in WT mice (FIG. 4D and FIG. 12E). Similarly, more mTOR proteins were co-localized with LAMP2 in CA1 apical dendrites of AS than WT mice (FIGS. 4C-D). The co-localization of p-mTOR (Ser2448) with LAMP2 was subsequently evaluated. More p-mTOR/LAMP2 double-stained puncta were observed in both soma and apical dendrites in hippocampal CA1 region of AS than in WT mice (FIGS. 4E-F and FIG. 12F).

Figure 13:
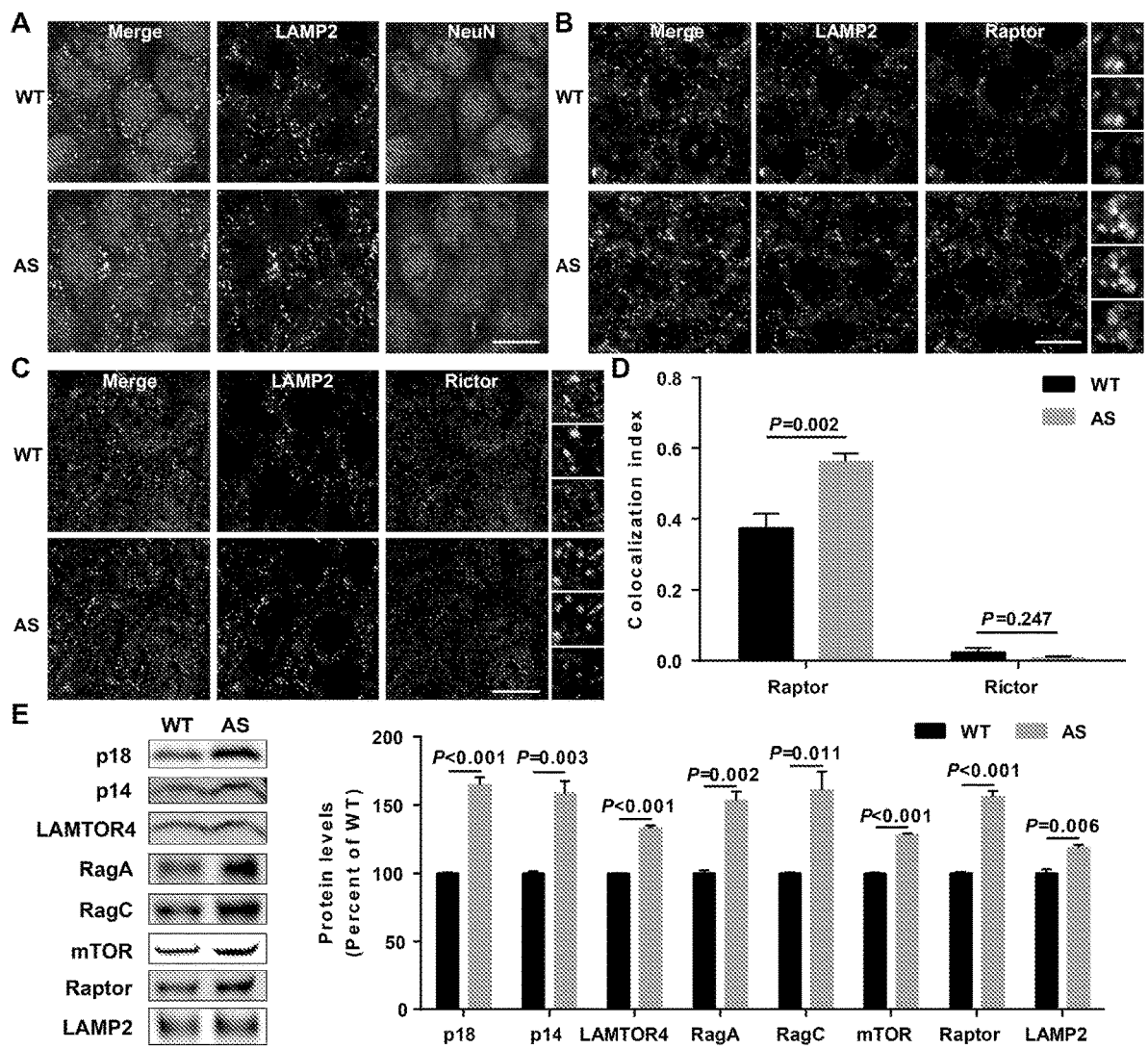
FIG. 13(A-E) shows lysosomal localization of Raptor and Rictor in hippocampus of WT and AS mice, and Western blot analysis of Ragulator-Rag complex as well as mTOR and Raptor in WT and AS hippocampal lysosome fractions. (A) Double staining of NeuN (red) and LAMP2 (green) in cell bodies of CA1 pyramidal neurons from WT and AS mice. Scale bar=10 µm. (B) Co-localization of Raptor (red) with LAMP2 (green) in cell bodies of CA1 pyramidal neurons from WT and AS mice. Scale bar=10 µm. (C) Co-localization of Rictor (red) with LAM P2 (green) in cell bodies of CA1 pyramidal neurons from WT and AS mice. Scale bar=10 µm. In B and C, insets show selected fields that were magnified ten times. (D) Quantification of Raptor-LAMP2 (n=6 mice, p=0.002), and Rictor-LAMP2 (n=6 mice, p=0.247) colocalization in cell bodies of CA1 pyramidal neurons from WT and AS mice. Unpaired t-test. (E) Left, Western blot analysis of p18, p14, LAMTOR4, RagA, RagC, mTOR, Raptor, and LAMP2 in enriched lysosomal fractions prepared from WT and AS hippocampus. Right, quantitative analysis of blots. Results are expressed as % of values in WT mice and shown as means±S.E.M. N=3 independent experiments, p<0.001 (p18), p=0.003 (p14), p<0.001 (LAMTOR4), p=0.002 (RagA), p=0.011 (RagC), p<0.001 (mTOR), p<0.001 (Raptor), and p=0.006 (LAMP2) (unpaired, two-tailed Student's t test).

To further confirm the lysosomal localization of mTORC1, the co-localization of Raptor with LAMP2 was examined. Raptor is a critical component of mTORC1 and serves as a scaffold to spatially position substrates in close proximity to mTOR (Hara et al., 2002; Kim et al., 2002; Nojima et al., 2003), and its binding to Rag GTPases is necessary and sufficient to activate mTORC1 (Sancak et al., 2008). Raptor was clearly co-localized with LAMP2 in CA1 pyramidal cell soma of adult mice, and more Raptor/LAMP2 double-stained puncta were detected in AS than in WT mice (FIGS. 13B and D). In contrast, Rictor, an essential component of mTORC2, showed no co-localization with LAMP2 in both WT and AS mice (FIG. 13C-D), suggesting that mTORC2 may not be recruited to lysosomes. Consistently, Western blot results showed that levels of the Ragulator-Rag complex as well as those of mTOR and Raptor were markedly increased in lysosomal fractions of hippocampus from AS mice, as compared to WT mice (FIG. 13E).

In addition to providing a platform for recruiting Rag GTPases and subsequently mTORC1 to lysosomes, p18 has also been shown to function as a RagA/B GEF, which facilitates the exchange of GDP from RagA/B to GTP (Bar-Peled et al., 2012). To test whether increased p18 levels in AS mice could lead to increased levels of GTP-bound RagA/B, the widely-used co-immunoprecipitation assay of p18 and RagA was used, based on the observation that GTP-bound RagA/B has a lower affinity for the Ragulator, as compared to GDP-bound RagA/B (Bar-Peled et al., 2012; Castellano et al., 2017). Co-immunoprecipitation results showed that levels of p18 immunoprecipitated by RagA antibodies were significantly lower in samples from AS mice, as compared to WT mice (FIG. 4G). Collectively, these results showed that increased p18 levels in hippocampus of AS mice facilitate lysosomal anchoring of the Ragulator-Rag complex and the activation of mTORC1 (see schematic in FIG. 4H).

Figure 5:
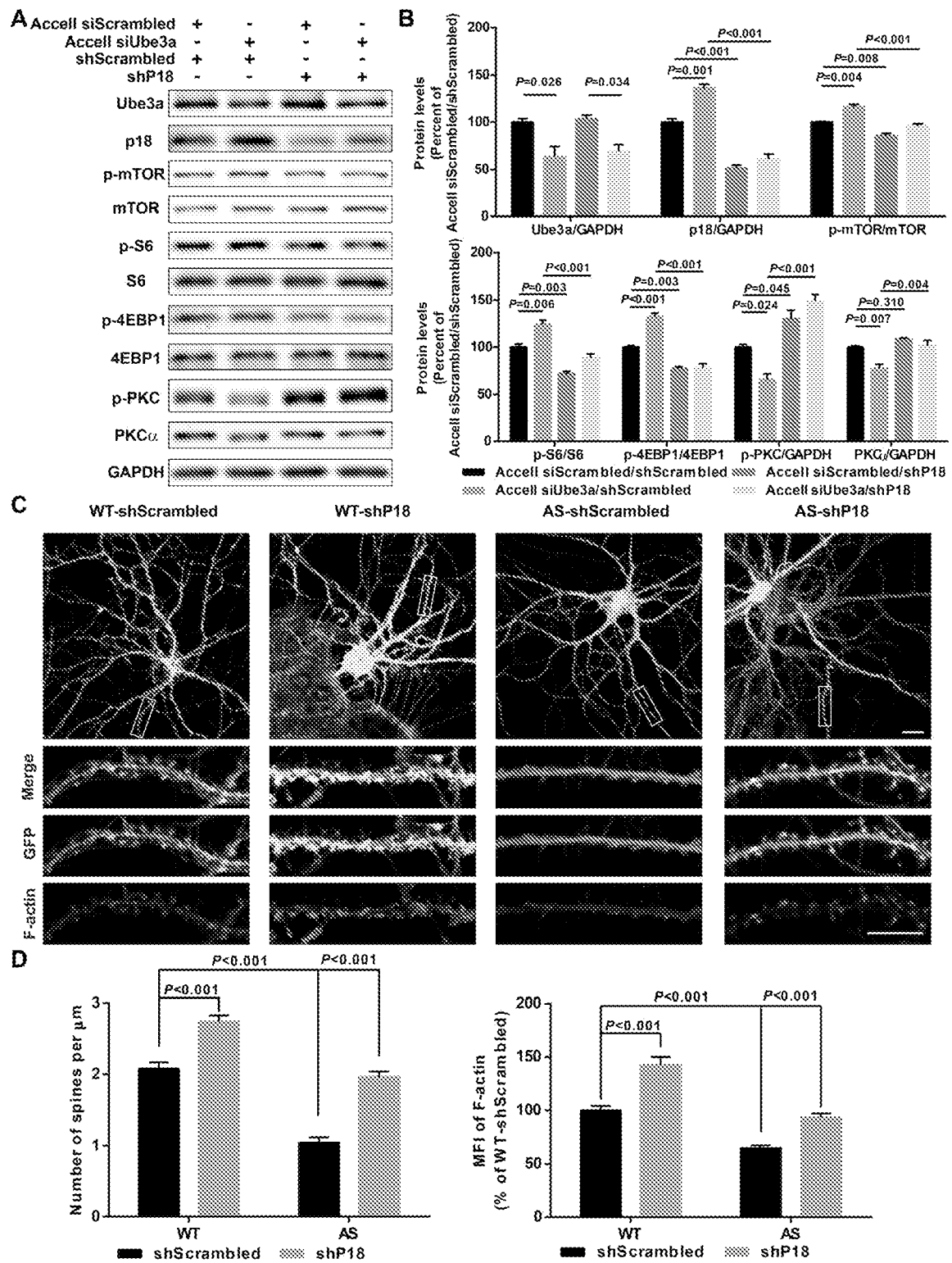
FIG. 5(A-D) shows that P18 mediates the effects of Ube3a on mTOR signaling, dendritic spine morphology, and actin polymerization. (A) Representative images of Western blots labeled with Ube3a, p18, p-mTOR, mTOR, p-S6, S6, p-4EBP1, 4EBP1, p-PKC, and PKCα (GAPDH as a loading control). Protein lysates from cultured hippocampal neurons transfected with the indicated constructs were prepared for Western blot analysis. (B) Quantitative analysis of blots shown in A. N=3 independent experiments, Accell siScrambled/shScrambled vs Accell siUbe3a/shScrambled, p=0.026 (Ube3a), p=0.001 (p18), p=0.004 (p-mTOR), p=0.006 (p-S6), p<0.001 (p-4EBP1), p=0.024 (p-PKC), p=0.007 (PKCα); Accell siScrambled/shScrambled vs Accell siScrambled/shP18, p<0.001 (p18), p=0.008 (p-mTOR), p=0.003 (p-S6), p=0.003 (p-4EBP1), p=0.045 (p-PKC), p=0.310 (PKCα); Accell siUbe3a/shScrambled vs Accell siUbe3a/shP18, p<0.001 (p18), p<0.001 (p-mTOR), p<0.001 (p-S6), p<0.001 (p-4EBP1), p<0.001 (p-PKC), p=0.004 (PKCα); Accell siScrambled/shP18 vs Accell siUbe3a/shP18, p=0.034 (Ube3a); two-way ANOVA with Tukey's post-test. (C) Representative images of F-actin (red) and GFP in cultured WT and AS hippocampal neurons (22 DIV) co-infected with GFP lentivirus and p18 shRNA or scrambled shRNA lentivirus. Scale bar, 20 μm (upper) or 10 μm (lower). (D) Quantitative analysis of images shown in C. N=9 neurons from at least 3 independent experiments, p<0.001, two-way ANOVA with Tukey's post-test. See also FIG. 14.

Example 5. P18 KD counteracts Ube3a deficiency-induced abnormal mTOR signaling and changes in dendritic spine morphology and actin polymerization in cultured hippocampal neurons. Whether reducing p18 levels could modify Ube3a deficiency-induced mTORC1 over-activation in cultured hippocampal neurons was directly tested. P18 expression was reduced by infection with a set of p18 shRNA lentiviruses, while Ube3a KD was achieved with Accell Ube3a siRNA (FIGS. 5A-B). Ube3a KD resulted in increased p18 levels (FIGS. 5A-B), in parallel with increased mTORC1 activation, as reflected by increased phosphorylation of mTOR and its downstream substrate S6 and 4EBP1, and decreased mTORC2 activation, as reflected by decreased (p−)PKCα levels. Increased mTORC1 activation and decreased mTORC2 activation were reversed by p18 KD (FIGS. 5A-B). These results strongly suggest that increased p18 levels contribute to Ube3a deficiency-induced abnormal mTOR signaling in AS mice. Importantly, p18 shRNA KD in the absence of Ube3a KD led to a reduction in mTORC1 activation and a concomitant increase in the activity of mTORC2 (FIGS. 5A-B), which further underscores the notion that mTOR signaling is very sensitive to changes in p18 levels.

Figure 14:
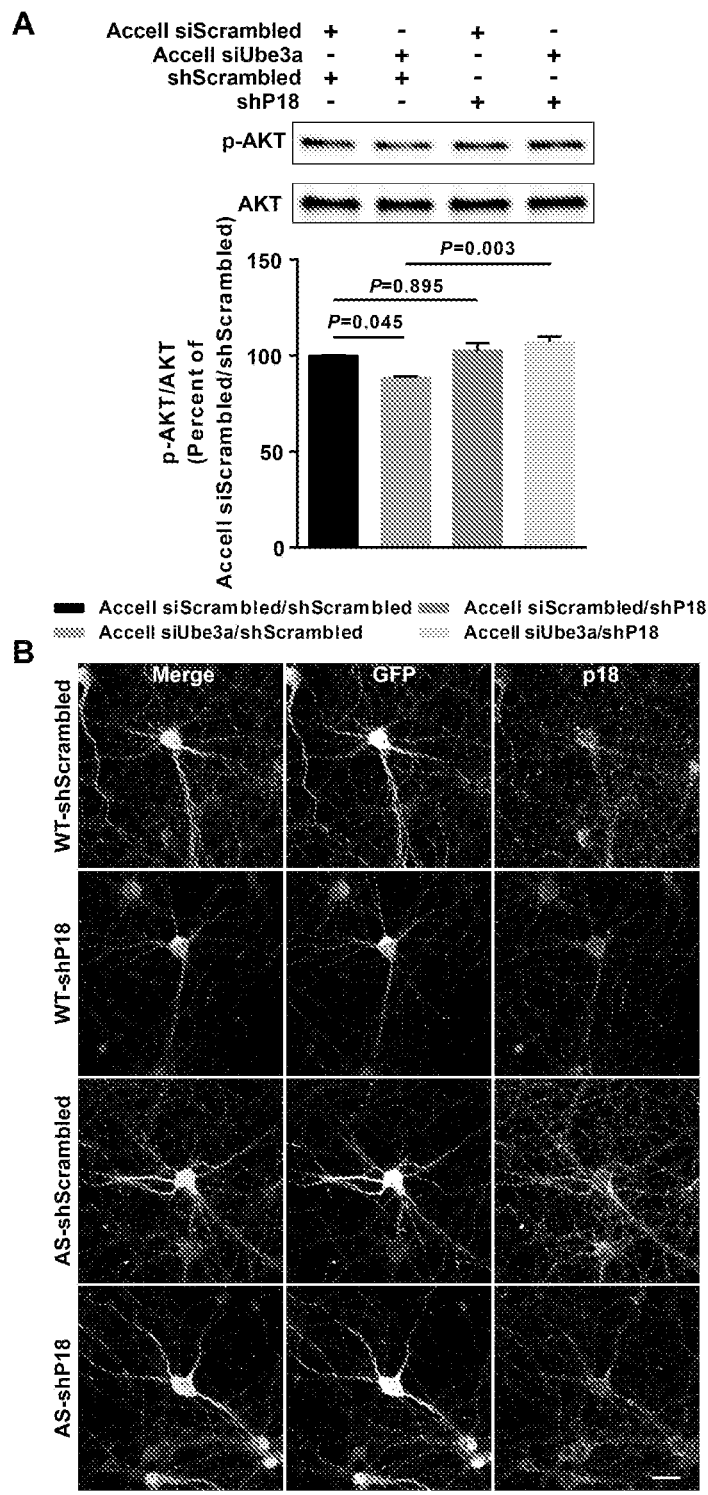
FIG. 14(A-B) shows effects of p18 knockdown in WT and AS hippocampal neurons. Representative images of p18 (red) and GFP in WT and AS hippocampal neurons co-infected with copGFP lentivirus and p18 shRNA or scrambled shRNA lentivirus. Scale bar, 30 µm.

Whether Ube3a-mediated p18 regulation could affect dendritic spine morphology and actin polymerization was also determined. Cultured hippocampal neurons from AS or WT mice were co-infected with p18 shRNA or control shRNA lentiviruses and a GFP control lentivirus, and actin polymerization was determined by staining for filamentous actin (F-actin). Confocal images of infected neurons indicated that p18 shRNA infection reduced p18 expression in cultured neurons from both WT and AS mice (FIG. 14). Neurons from AS mice exhibited reduced dendritic spine density and actin polymerization, as compared to neurons from WT mice (FIGS. 5C-D). P18 shRNA KD increased spine density and restored actin polymerization in neurons from AS mice, and slightly enhanced spine density and F-actin levels in neurons from WT mice (FIGS. 5C-D). These results indicate that deficiency in Ube3a-mediated p18 degradation contributes to spine defects and actin polymerization abnormality in neurons from AS mice. The effects of p18 KD on spine maturation was further analyzed in in vivo studies presented in the following sections.

Figure 15:
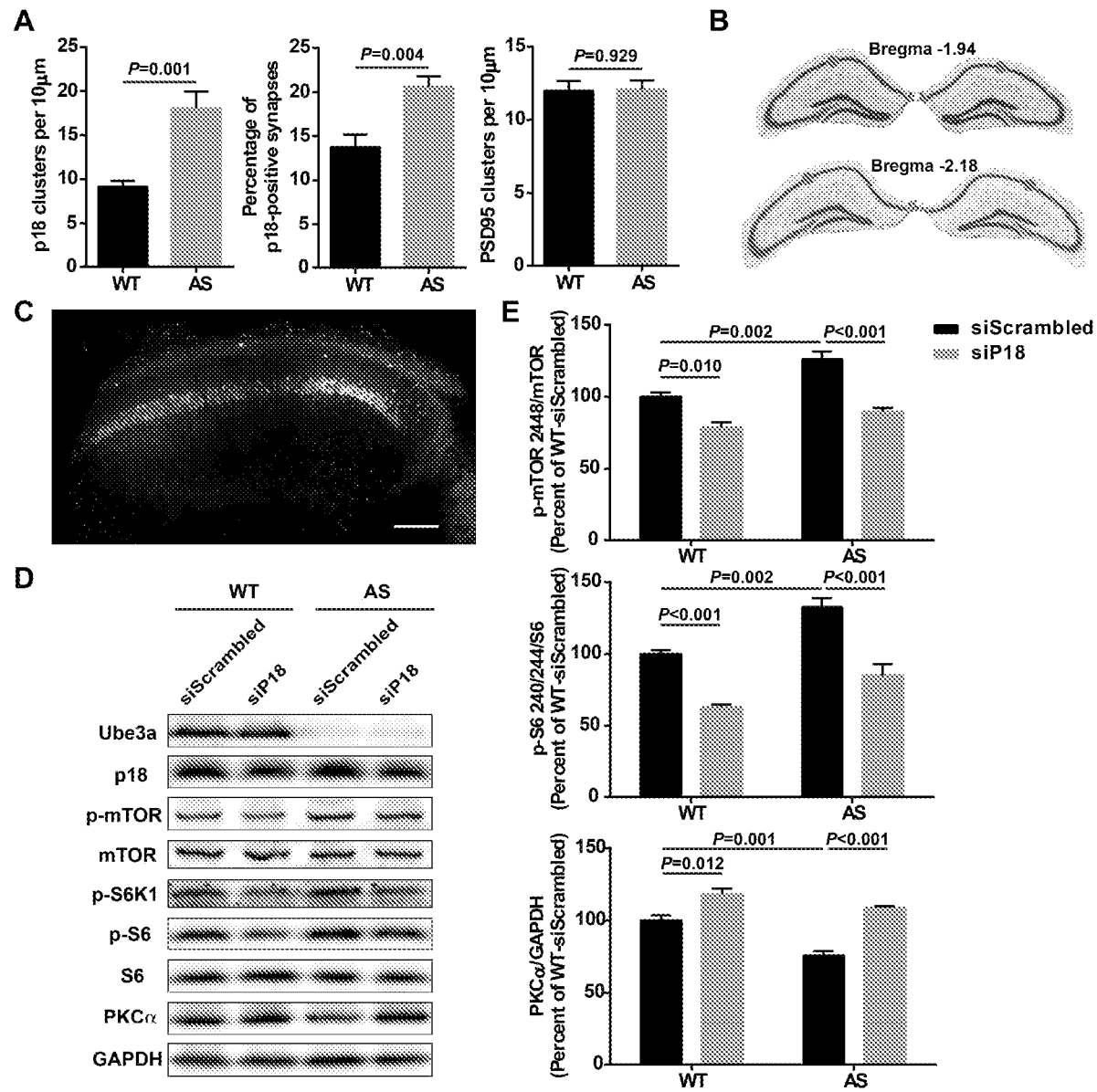
FIG. 15(A-E) shows effects of p18 knockdown in hippocampal CA1 region on mTOR signaling in WT and AS mice. (A) Quantitative analysis of the number of p18-(left, p=0.001) and PSD95-immunoreactive puncta (right, p=0.929), as well as percentage of p18 and PSD95 dually stained puncta/synapses (middle, p=0.004) in hippocampal CA1 region. N=6 mice, unpaired t-test. These data are paired with FIG. 6A. (B) The coordinates of the injection sites were (mm): AP −1.94, ML ±1.4, DV−1.35 from Bregma; AP −2.2, ML ±1.8, DV −1.5 from Bregma, in the CA1 region of hippocampus and are indicated by red circles. (C) Representative tile scan confocal image of GFP expression in hippocampal CA1 region 4 weeks following injection of AAV with GFP reporter gene. Scale bar=200 µm. (D) Representative images of Western blots labeled with Ube3a, p18, p-mTOR, mTOR, p-S6K1, p-S6, S6, and PKCα (GAPDH as a loading control). Protein lysates from hippocampal CA1 region infected with the indicated AAV were prepared for Western blot analysis. (E) Effects of p18 knockdown in hippocampal CA1 region on mTOR signaling in WT and AS mice. For p-mTOR, p=0.010, WT-siScrambled vs WT-siP18, p=0.002, WT-siScrambled vs AS-siScrambled, p<0.001, AS-siScrambled vs AS-siP18; For p-S6, p<0.001, WT-siScrambled vs WT-siP18, p=0.002, WT-siScrambled vs AS-siScrambled, p<0.001, AS-siScrambled vs AS-siP18; For PKC, p=0.012, WT-siScrambled vs WT-siP18, p=0.001, WT-siScrambled vs AS-siScrambled, p<0.001, AS-siScrambled vs AS-siP18; n=4 mice for WT-siScrambled, WT-siP18, and AS-siScrambled, n=3 mice for AS-siP18, two-way ANOVA with Tukey's post-test.

Example 6. P18 KD promotes LTP and stimulates dendritic spine maturation in AS mice. High magnification confocal images of adult hippocampal CA1 pyramidal neurons revealed that in addition to being co-localized with lysosomal markers, p18 was also localized in the vicinity of and often co-localized with PSD95 (arrowheads in FIG. 6A). Quantitative analysis showed that the number of p18-immunoreactive puncta was markedly increased in AS mice (FIG. 15A). Furthermore, the percentage of PSD95-stained puncta labeled with p18 antibodies was also significantly increased in AS mice compared to WT mice (FIG. 15A), although there was no significant difference in the overall number of PSD95-immunopositive puncta between AS and WT mice (FIG. 15A). To determine whether increased synaptic p18 levels could contribute to impaired functional and structural synaptic plasticity in AS mice, we performed in vivo p18 siRNA KD experiments.

AAV vectors containing p18 siRNA or scrambled siRNA (control) were bilaterally injected into the dorsal hippocampal CA1 region of WT and AS mice (FIG. 15B), and LTP in hippocampal slices was analyzed 4 weeks later from these 4 experimental groups. To evaluate infection efficiency, GFP expression, as well as p18 levels were determined in hippocampal slices by immunohistochemistry following LTP recording (FIG. 6B). Only mice that exhibited significant GFP expression in the CA1 region (FIG. 15C) were included in the LTP and spine analyses. Quantitative analysis showed that p18 expression was significantly increased in AS mice, as compared to WT mice, and this increase was reversed by p18 siRNA infection (FIG. 6C). P18 siRNA infection also significantly reduced p18 expression in WT mice, to a larger degree than in AS mice (FIG. 6C). Levels of p18, p-mTOR/mTOR, p-S6/S6, and PKCα in CA1 regions were also determined using Western blots; p18 KD reduced mTORC1 activity and increased mTORC2 activity in both WT and AS mice (FIGS. 15D-E).

Figure 16:
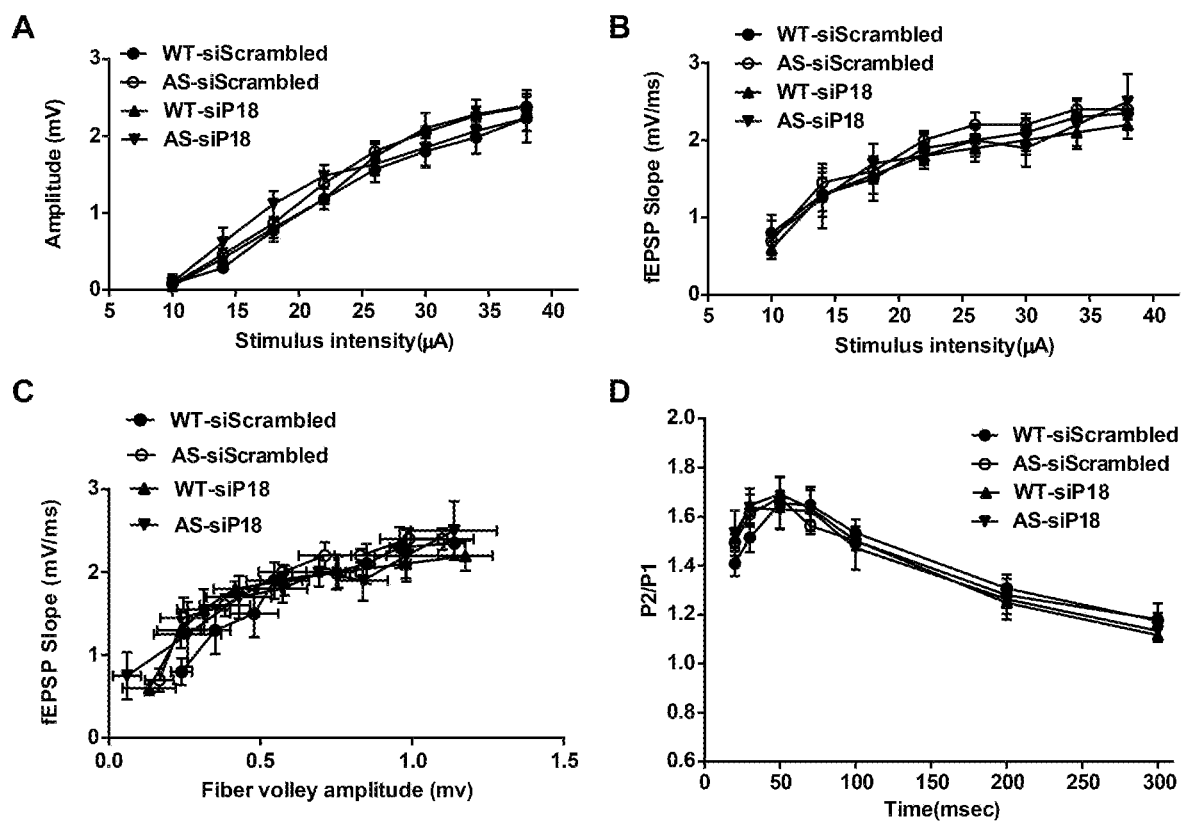
FIG. 16(A-D) shows effects of p18 knockdown in hippocampal CA1 region on input/output curves and paired-pulse facilitation in WT and AS mice. Related to FIG. 6. (A-C) Input/output curves. Amplitudes of field EPSPs (A) and the slope of the field EPSP (B) were determined for various intensities of stimulation. (C) Relationship between the slope of the evoked fEPSPs and the corresponding fiber volley amplitude. The results are means±S.E.M.; n=3 mice; there were no significant differences among the 4 groups of mice. (D) Paired-pulse facilitation. The amplitude of the second response of a paired-pulse was calculated as a percent of the amplitude of the first response for various inter-pulse intervals. The results are means±S.E.M.; n=5 mice; there were no significant differences among the 4 groups of mice.

Baseline synaptic responses, including input/output curves (I/O curves) and paired pulse facilitation, were not altered by control siRNA or p18 siRNA in either AS or WT mice (FIG. 16). LTP was induced by applying theta-burst stimulation (TBS) to Schaffer collaterals in the CA1 region, as previously described (Baudry et al., 2012; Sun et al., 2015b). TBS elicited typical LTP in field CA1 of hippocampal slices from control siRNA-injected WT mice, whereas it only elicited a transient facilitation in slices from control siRNA-injected AS mice (FIGS. 6D-E), a result similar to that found in slices from untreated AS mice (Baudry et al., 2012; Sun et al., 2015b). In contrast, bilateral CA1 injection of p18 siRNA enhanced TBS-elicited LTP in hippocampal slices from AS mice (FIGS. 6D-E), while it reduced TBS-induced LTP in slices from WT mice (FIGS. 6D-E).

Figure 7:
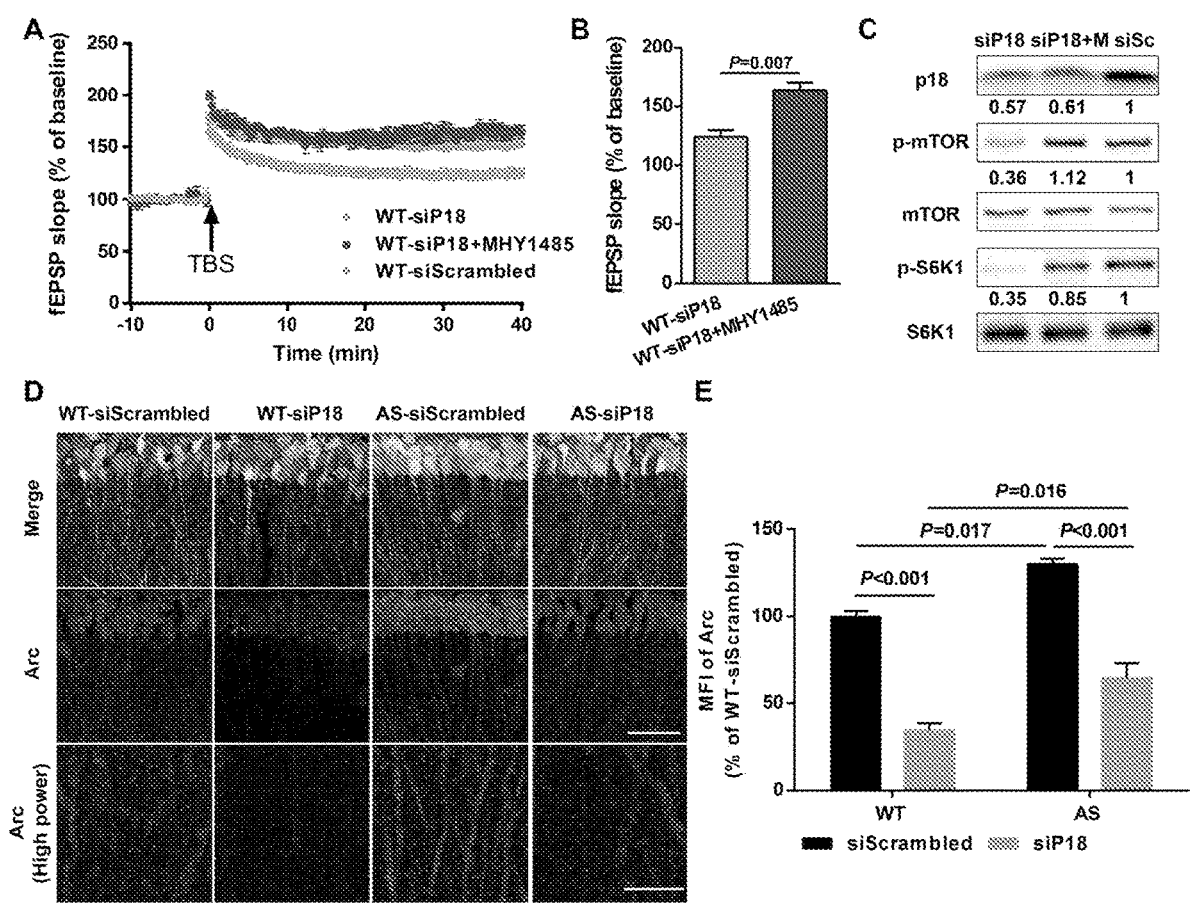
FIG. 7(A-E) shows that P18 KD impairs LTP in WT neurons due to its over-inhibition of mTORC1 activity and Arc levels. (A-C) Effects of MHY1485 treatment on LTP in p18 siRNA-injected WT mice. (A) Slopes of fEPSPs were normalized to the average values recorded during the 10 min baseline. (B) Means±S.E.M. of fEPSPs measured 40 min after TBS in different groups. N=3-14 slices from 3-8 mice, p=0.007, unpaired t-test. (C) Representative Western blots showing the relative abundance of p18, p-mTOR/mTOR, and p-S6K/S6K in lysates from control siRNA (siSc) or p18 siRNA (siP18)-infected WT hippocampal slices. Slices were treated with or without MHY1485 (M). (D-E) Effects of Ube3a deficiency and p18 KD in hippocampal CA1 region on Arc expression. (D) Representative images of CA1 pyramidal neurons stained with anti-Arc (red) and -GFP (green) antibodies. Scale bar=50 μm (low power images) and 10 μm (high power images). (E) Quantitative analysis of the MFI of Arc-immunoreactivity of CA1 pyramidal neurons (means±S.E.M. of 3 slices from 3 different animals; p<0.001, WT-siScrambled vs WT-siP18; p=0.017, WT-siScrambled vs AS-siScrambled; p<0.001, AS-siScrambled vs AS-siP18; p=0.016, WT-siP18 vs AS-siP18, two-way ANOVA with Tukey's post-hoc analysis).

To determine whether reduced LTP in p18 siRNA WT group was due to reduced mTORC1 activation because of "below normal" p18 levels, we used an mTOR activator MHY1485. Pre-incubation of hippocampal slices with MHY1485 (2 µM) for 60 min reestablished TBS-elicited LTP to levels identical to those in control siRNA-injected WT mice (FIGS. 7A-B). Levels of p18, p-mTOR/mTOR, and p-S6K1/S6K1 in AAV infected regions were determined using Western blots; p18 KD-induced reduction of mTORC1 signaling in WT mice was reversed by acute treatment with MHY1485 (FIG. 7C). Arc levels in CA1 dendritic field injected with control or p18 siRNA were also analyzed, since Arc is a well-known downstream effector of Ube3a and/or mTOR signaling (Greer et al., 2010; Sun et al., 2016). As expected, levels of Arc were significantly higher in control siRNA-injected AS mice as compared to control siRNA-injected WT mice; p18 KD significantly reduced Arc expression in both WT and AS hippocampal slices (FIGS. 7D-E). Of note, p18 KD induced a larger reduction in Arc expression in WT mice than in AS mice (FIGS. 7D-E), which may contribute to reduced LTP in p18 siRNA WT group. Together, these results suggest that p18-mediated regulation of Arc levels is critical for LTP in WT and AS mice.

Figure 17:
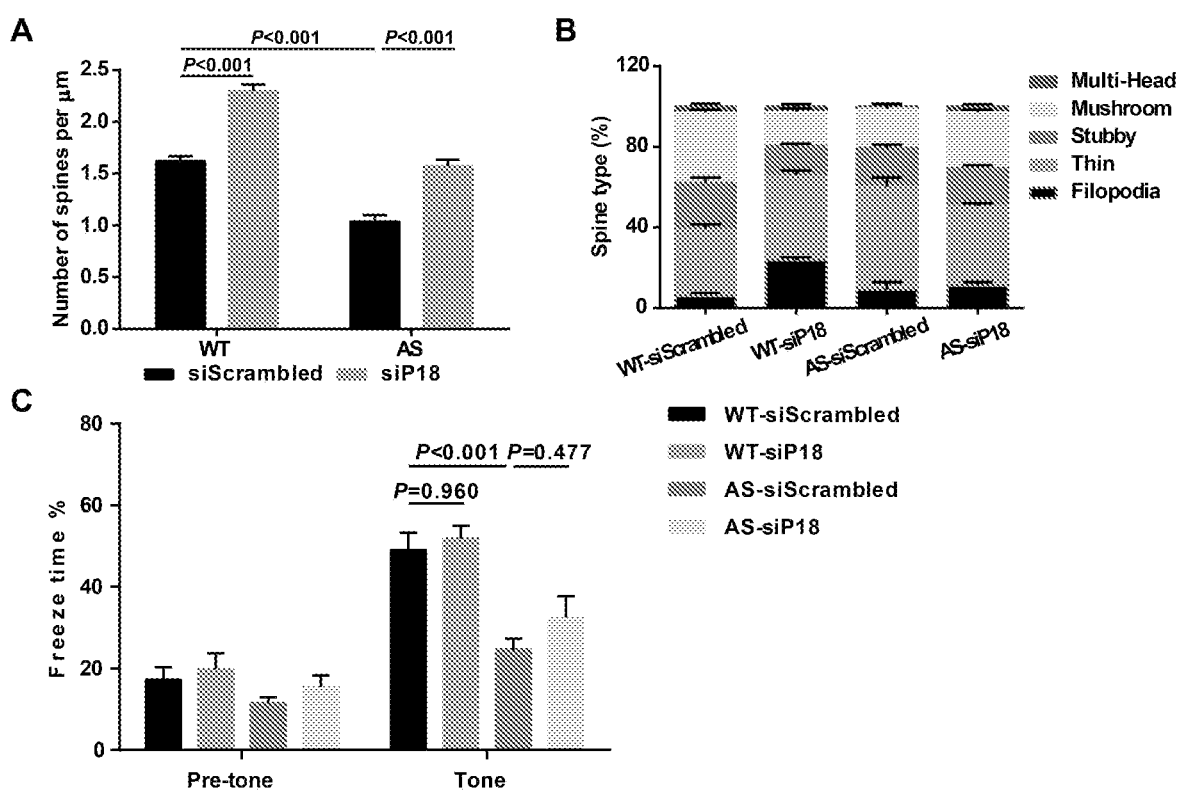
FIG. 17(A-C) shows effects of p18 knockdown in hippocampal CA1 region on dendritic spine number and the proportion of various spine types as well as tone memory in WT and AS mice. (A) Quantitative analysis of dendritic spine density shown in FIG. 7A (means±SEM from 10 slices). P<0.001, two-way ANOVA with Tukey's post-test.

Golgi staining in hippocampal CA1 region of WT and AS mice injected with p18 siRNA or control siRNA was performed. As previously reported (Dindot et al., 2008; Sun et al., 2016), spine density was lower with a higher proportion of immature spines (thin or filopodia) in AS mice, as compared with WT mice (FIGS. 8A-B and FIG. 17(A-B)). P18 KD significantly increased the number of mature dendritic spines in hippocampal pyramidal neurons of AS mice, while it increased the number and proportion of immature dendritic spines of WT mice (FIGS. 8A-B and FIG. 17(A-B)). The effects of p18 KD on the number of mature dendritic spines (FIG. 8B) correlated well with the effects on LTP. As an independent means of assessing the effect of changes in spine morphology, we recorded miniature excitatory postsynaptic currents (mEPSCs) from WT and AS hippocampal pyramidal neurons in acute slice preparations. A reduction in the frequency and no change in the amplitude of mEPSCs in AS neurons, as compared to WT neurons (FIGS. 8C-D) was observed.

Figure 8:
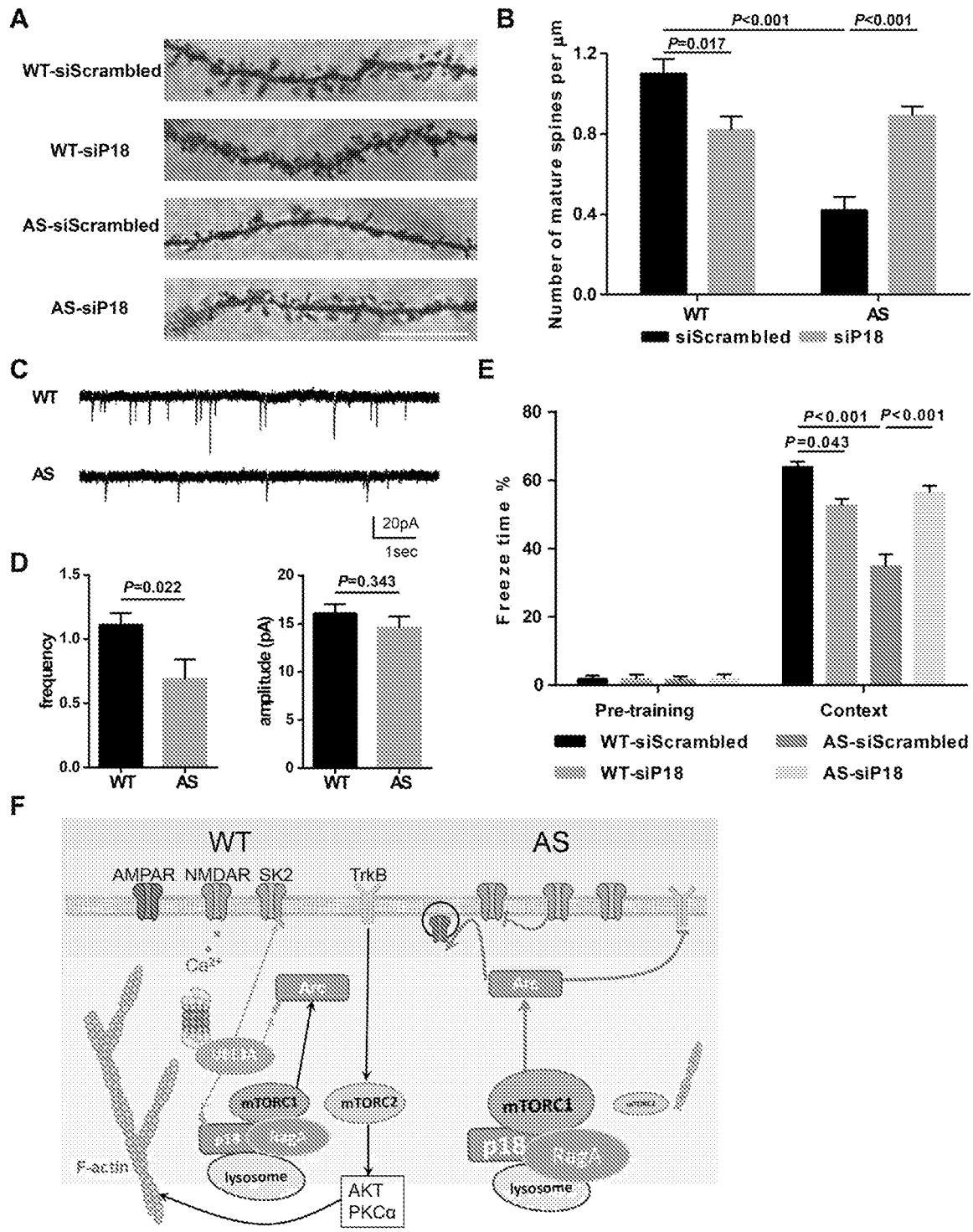
FIG. 8(AF) shows effects of Ube3a deficiency and p18 KD in hippocampal CA1 region on dendritic spine morphology, mEPSCs, and fear-conditioning memory. (A) Representative light micrograph images from Golgi-impregnated CA1 pyramidal neurons. Scale bar=10 μm. (B) Quantitative analysis of mature dendritic spine (multi-head, mushroom, and stubby spines) density shown in A (means±SEM from 10 slices). p=0.017, WT-siScrambled vs WT-siP18; p<0.001, WT-siScrambled vs AS-siScrambled; p<0.001, AS-siScrambled vs AS-siP18, two-way ANOVA with Tukey's post-test. (C) Representative mEPSC traces recorded in hippocampal neurons from WT and AS slices. Scale bar, 20 pA/1 s. (D) Quantification of mEPSC frequency (p=0.022) and amplitude (p=0.343) from WT (n=12) and AS (n=7) mice. Student's t test. (E) % freezing for different experimental groups in context memory (means±S.E.M. of 6-mice; p=0.043, WT-siScrambled vs WT-siP18; p<0.001, WT-siScrambled vs AS-siScrambled; p<0.001, AS-siScrambled vs AS-siP18, two-way ANOVA with Tukey's post-hoc analysis). (F) Model for Ube3a-mediated regulation of synaptic plasticity (see text for details). See also FIG. 17.

Example 7. P18 KD improves learning and memory performance of AS mice in the fear-conditioning paradigm. To determine whether p18 KD could also ameliorate the impairment in hippocampus-dependent learning in AS mice, fear conditioning in AS and WT mice 8 weeks after AAV injection was analyzed. AS mice were impaired in context- and tone-dependent fear-conditioning, and p18 KD in the CA1 region significantly enhanced context-dependent learning performance, while it did not affect tone-dependent learning in AS mice (FIG. 8E and FIG. 17C). Consistent with its effects on LTP and spine morphology, p18 siRNAs treatment reduced context-dependent learning performance in WT mice (FIG. 8E). There was no difference in freezing time during the pre-conditioning period, or before tone application in the testing period between all experimental groups (FIG. 8E and FIG. 17C). Bilateral-intrahippocampal p18 knockdown by AAV-sip18 significantly improved the performance of AS mice in context learning and reduced ARC expression in hippocampus.

Figure 6:
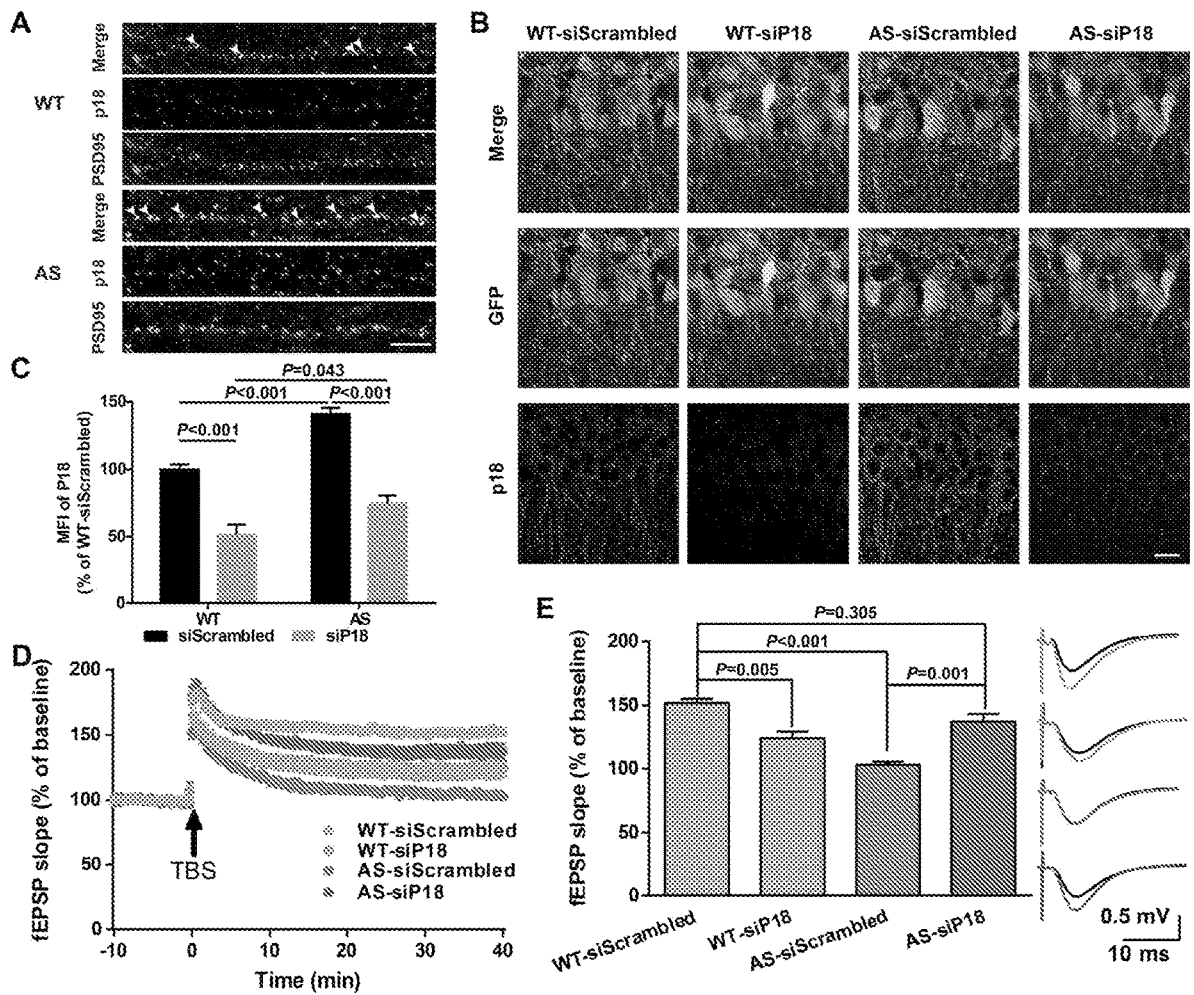
FIG. 6(A-E) shows effects of p18 KD in hippocampal CA1 region on LTP in WT and AS mice. (A) Representative images of dendrites of CA1 pyramidal neurons stained with anti-p18 (red) and -PSD95 (green) antibodies. Arrowheads indicate co-localized puncta. Scale bar=10 μm. (B) Representative images of CA1 pyramidal neurons stained with anti-p18 (red) and -GFP (green) antibodies. Scale bar=20 μm. (C) Quantitative analysis of the mean fluorescence intensity (MFI) of p18-immunoreactive puncta in GFP-positive CA1 pyramidal neurons. N=6 mice, p<0.001, WT-siScrambled vs WT-siP18; p<0.001, WT-siScrambled vs AS-siScrambled; p<0.001, AS-siScrambled vs AS-siP18; p=0.043, WT-siP18 vs AS-siP18, two-way ANOVA with Tukey's post-test. (D-E) Effects of AAV siRNA-mediated p18 KD on LTP in WT and AS mice. (D) Slopes of fEPSPs were normalized to the average values recorded during the 10 min baseline. (E) Means±S.E.M. of fEPSPs measured 40 min after TBS in different groups. N=7-14 slices from 4-8 mice, p=0.005, WT-siScrambled vs WT-siP18, p<0.001, WT-siScrambled vs AS-siScrambled, p=0.001, AS-siScrambled vs AS-siP18, p=0.305, WT-siScrambled vs AS-siP18, two-way ANOVA with Tukey's post-test. Inset shows representative traces of evoked fEPSPs before and 40 min after TBS. Scale bar 0.5 mV/10 ms. See also FIG. 15 and FIG. 16.

Example 8. Bilateral intrahippocampal p18 knockdown by AAV-sip18 significantly improved the performance of AS mice in context learning but not in cue learning. In this study, knockdown RNA was delivered by specific intrahippocampal injection. On the other hand, AAV-sip18-injected WT mice exhibited reduced performance in context learning, a result matching the result obtained on hippocampal LTP. Image analyses show that ARC levels were significantly reduced in AAV-sip18-injected hippocampi in AS mice and more so in WT mice, which correlated well with changes in p18 levels, as shown in FIG. 6. More importantly, the changes in context learning correlated well with those in ARC levels in the CA1 region. It is noteworthy that hippocampal ARC levels in AAV-sip18-injected WT mice were significantly lower than in AAV-sip18-injected AS mice, which probably contributes to the impairment in LTP and context learning observed in these mice. Regarding the question of why AAV-sip18 injection induced a larger reduction in p18 levels in WT than in AS mice, it may be due to the fact that in AS mice, p18 degradation is much reduced, as compared to WT mice due to the lack of Ube3a. The larger reduction in p18 levels in AAV-sip18-injected WT mice could thus account for the larger reduction in ARC levels and for impaired LTP and learning in these mice. These data may also fit well with results in the literature indicating that Ube3a deficiency results in AS, while its overexpression is a major risk factor for autism, which suggests that too much or too little of Ube3A and its substrates are detrimental for typical function.

Example 9: Short peptides targeting p18 reduced mTOR activation and promoted peripheral positioning of lysosomes in HELA cells. To test whether blocking p18 ubiquitination and interruption of its interaction with other proteins could disrupt mTOR signaling and lysosome localization and function, we designed two small decoy peptides (TAT-2031 and TAT-151) targeting different domains of p18 containing lysine residues (FIG. 20A); these peptides are conjugated to the cell membrane transduction domain of HIV-1 Tat protein. The results showed that TAT-2031 significantly reduced mTORC1 activation (FIG. 20C) and increased lysosome distribution to the peripheral region of the cell (FIG. 20B). Table 3 summarizes the results with the peptides. SEQ ID NO:19 corresponds to KLLLDPSSPPTK, residues 20-31 of p18.

TABLE 3

| Effects | TAT (YGRKKRR QRRR) (SEQ ID NO: 20) | TAT-2031 (YGRKKRRQRRR KLLLDPSSPPTK) (SEQ ID NO: 21) | TAT-151 (YGRKKRRQR RRKEELVV) (SEQ ID NO: 22) |
|---|---|---|---|
| mTOR signaling pathway | No effect | Reduced the ratio of p-mTOR/mTOR, p-S6K1/S6K1, and p-S6/S6 | Little effect |
| Lysosome positioning in Hela cell | No effect | Shifted the distribution of lysosomes toward the cell periphery | Not studied |
| p18-TRPML1 interaction | No effect | Reduced the interaction | Not studied |
| Migration of Hela cell | No effect | Slightly reduced the migration | Not studied |

FIG. 20A provides the amino acid sequence of p18 (SEQ ID NO:23).

Example 10: P18 regulates dendritic trafficking and positioning of lysosomes in cultured mouse hippocampal neurons. Primary hippocampal neurons (DIV7+14) were infected with viral vectors containing either p18 shRNA (shP18) or scrambled shRNA (shSc) and GFP (green). They were stained with LysoTracker (Red), and live imaged every second for 1 min to visualize lysosomal trafficking in dendrites. Vesicles were manually classified according to their movement in a blinded fashion. Lysosome distribution along the proximal dendrites and overall percent of lysosome moving in anterograde vs. retrograde direction was quantified. The results show that p18 deletion increases the mobility of lysosomes in both the anterograde and retrograde direction. See FIG. 21. They also show that such deletion results in an accumulation of lysosomes in the proximal dendrites. Thus, one of the functions of p18 is to limit the mobility of lysosomes and to maintain a more homogenous distribution of lysosomes in the dendrites. Conversely, interfering with p18 function could result in modifications of lysosome mobility and distribution within dendrites.

The last decade has witnessed a rapid growth in knowledge of amino acid-mediated regulation of mTORC1 signaling, including the identification of a lysosome-based platform for its activation. Although it has been shown that p18 has a critical role in stabilization of the Ragulator-Rag complex (de Araujo et al., 2017) and anchoring it to lysosomes, little is known regarding the regulation of p18 levels. The above results provide several lines of evidence indicating that Ube3a is an E3 ligase for p18, and that Ube3a-mediated p18 ubiquitination leads to its degradation by the proteasome. Of note, p18 myristoylation and lysosomal localization of p18 were required for its ubiquitination and mTORC1 activation, suggesting that Ube3a specifically targets lysosomal-localized p18, thereby efficiently regulating lysosome-based mTORC1 activation.

Although regulation of mTORC1 by the TSC complex-Rheb axis is well documented in the CNS, compared with various cell lines, its regulation by a lysosome-anchored platform has rarely been studied. The above results showed for the first time that, in hippocampal neurons, p18 is essential for lysosomal localization of other Ragulator members and Rag GTPases, as p18 KD markedly reduced the lysosomal localization of these proteins, which is in agreement with that reported in other cell types (Nada et al., 2009; Sancak et al., 2010). It is further shown that lysosomal localization of the Ragulator-Rag complex is essential for mTORC1 activation in hippocampal neurons. Additionally, it is shown that lysosomal localization and mTORC1 activation depends on Ube3a-mediated regulation of p18 levels, as a Ube3a deficiency-induced increase in p18 levels enhanced lysosomal recruitment of the Ragulator-Rag complex, leading to mTORC1 over-activation. The results herein also support the idea that the Ragulator functions not only as a platform but also as a Rag GTPase GEF to facilitate mTORC1 activation (Bar-Peled et al., 2012). Furthermore, p18 KD reversed Ube3a deficiency-induced increase in mTORC1 activation and decrease in mTORC2 activation. Collectively, these results indicate that Ube3a-mediated p18 ubiquitination and degradation are critical for maintaining an optimal level of lysosome-anchored Ragulator-Rag complex and mTORC1 activation in hippocampal neurons.

The functional roles of lysosome-based/p18-dependent regulation of mTOR signaling in hippocampal neurons continues to be studied. In contrast to the classical notion that lysosomes are mostly localized in neuronal soma and function merely as a 'recycling device', recent studies have shown that lysosomes are enriched in dendrites and that activity-dependent release of lysosomal hydrolases plays important roles in synaptic plasticity (Goo et al., 2017). It is shown here that p18 was not only co-localized with lysosome markers, but was also present in the vicinity of or co-localized with PSD95-labeled synapses in apical dendrites of hippocampal CA1 pyramidal neurons. This localization enables p18 to rapidly assemble or disassemble lysosome-based platforms for mTORC1 activation, and to possibly regulate other enzymes (e.g. MARK), in the vicinity of synapses, thereby regulating synaptic plasticity. The above results also underscored the importance of maintaining optimal p18 levels, as both 'too much' and 'too little' p18 resulted in abnormal spine structure and synaptic plasticity. Specifically, it is shown that Ube3a deficiency-induced increase in p18 levels was associated with increased mTORC1 activation, decreased spine maturation, and impaired LTP and learning performance, all of which were reversed by p18 KD. On the other hand, p18 KD in WT mice resulted in an increased number of immature spines, LTP impairment, and reduced learning performance, possibly because of decreased mTORC1 signaling, as an mTORC1 activator rescued p18 KD-induced LTP impairment. Different levels of mTORC1 inhibition could also explain why in our previous study rapamycin treatment improved LTP and spine maturation in AS mice, but did not affect either LTP or spine morphology in WT mice (Sun et al., 2016). Along this line, work from the Costa-Mattioli lab clearly indicated that a low concentration of rapamycin has no effect on LTP, while a high concentration of rapamycin impairs LTP in WT mice (Stoica et al., 2011). Similarly, it has been reported that although ErbB inhibitors enhanced contextual fear memory in AS mice, they impaired long-term memory in WT mice (Kaphzan et al., 2012).

Several downstream mechanisms could account for the effects of different levels of p18-mTORC1 signaling in synaptic plasticity and learning and memory (see schematic in FIG. 8F). First, activation of mTORC1-dependent local protein synthesis could account for the increased levels of the immediate-early gene product, Arc in AS mice reported by us and other groups (Cao et al., 2013; Greer et al., 2010; Sun et al., 2016). p18 KD reduced Arc immunoreactivity in CA1 pyramidal neurons, possibly through inhibition of the mTORC1-S6K1 pathway, as was the case with rapamycin treatment (Sun et al., 2016). Arc is known to induce AMPAR endocytosis, which dampens LTP expression and favors LTD induction (Chowdhury et al., 2006; Rial Verde et al., 2006). Related to this, both NMDAR-dependent and mGluR-dependent LTD in hippocampus are enhanced in AS mice (Pignatelli et al., 2014; Sun et al., 2015b). Increased Arc levels have been found to impair TrkB-PSD95 signaling in AS mice (Cao et al., 2013). On the other hand, inhibition of mTORC1 activity could also inhibit spine maturation, as mTORC1 activation has been shown to interact with other local synaptic events to promote spine enlargement (Henry et al., 2017).

Second, ample evidence has indicated that the dynamic properties of actin networks are crucial for synaptogenesis and synaptic plasticity; LTP consolidation is accompanied by increased levels of F-actin (Krama'r et al., 2006; Lin et al., 2005). mTORC2 activity, which is reduced by mTORC1-mediated feedback inhibition in AS mice (Sun et al., 2015a), has been shown to be crucial for actin polymerization (He et al., 2013; Huang et al., 2013; Jacinto et al., 2004; Sun et al., 2016; Thomanetz et al., 2013). LTP impairment in AS mice was associated with reduced TBS-induced actin polymerization, compared with WT mice, and this reduction could be ameliorated by either a positive AMPAR modulator or a SK2 channel blocker (Baudry et al., 2012; Sun et al., 2015b). Both compounds increase NMDAR activity and Ca2+ influx, thereby activating signaling proteins (e.g. CamKII, PKA, Rho), which facilitate F-actin formation. Similarly, reducing inhibitory inputs to CA1 pyramidal neurons using an ErbB inhibitor (Kaphzan et al., 2012), could also facilitate the activation of these signaling pathways and spine remodeling. p18 KD increased mTORC2 activity, resulting in actin polymerization and spine maturation, albeit through different downstream signaling pathways (activation of PKCa and Akt, etc.). Conditional deletion of Rictor in the postnatal murine forebrain greatly reduced mTORC2 activity and dendritic spine density in CA1 pyramidal neurons (Huang et al., 2013). Finally, p18 has been shown to directly interact with p27 (kip1), thereby regulating RhoA activity and actin remodeling (Hoshino et al., 2011), and autophagic activity (Zada et al., 2015). Whether these mTOR-independent p18 functions play any role in synaptic plasticity and brain development remains to be determined. Of note, baseline synaptic transmission and paired-pulse facilitation were not altered by p18 KD in both WT and AS mice, indicating that changes in synaptic plasticity resulting from p18 KD are likely a result of postsynaptic modifications related to processes that promote actin filament assembly during the minutes following TBS. The above results also indicated that, while there was a significant reduction in the frequency of mEPSCs in AS mice, mEPSC amplitude was not different from that found in WT mice, a result in agreement with that of Greer et al. (2010), but not that of Kaphzan et al. (2012). This pattern would be consistent with a loss of mature spines and the existence of a relatively normal AMPA receptor density in the remaining intact spines of pyramidal neurons of AS mice.

Deregulation of mTOR signaling has been identified as a phenotypic feature common to various forms of ASD, including fragile X syndrome, and mutations in tuberous sclerosis complex 1 and 2 (TSC1/2), neurofibromatosis 1, and phosphatase and tensin homolog (PTEN) (Huber et al., 2015). In contrast to the above findings, Tang et al. (2014) recently reported that over-activation of mTORC1 in TSC2+/− ASD mice resulted in increased spine density because of inhibition of the autophagy that underlies postnatal spine pruning. However, to date there is no report indicating that there is decreased autophagy in AS mice, suggesting the existence of different mechanisms downstream of mTORC1 in these two different mouse models. Although mTOR signaling is increased in Fragile X mouse models, a recent report showed that chronic rapamycin treatment did not reverse behavioral phenotypes and had adverse effects on sleep and social behavior in both control and Fmr1 KO mice (Sue' et al., 2017). These results strengthen the notion that further understanding of the mTOR pathway and its upstream and downstream regulation is needed.

Although it is proposed that Ube3a-mediated regulation of the p18-mTOR pathway is crucial in the pathogenesis of AS, the above results by no means intends to conclude that p18 is the sole Ube3a target implicated in AS. Rather, the results indicate that the newly identified regulation of mTORC1 activation by lysosome-located p18 is present in the brain and plays important roles in synaptic plasticity, and document the existence of another layer of regulation in the already complex mTOR pathway, namely the regulation of p18 levels by Ube3a. Importantly, while UBE3A deficiency results in AS, UBE3A over-expression results in increased ASD risk. Increased density of dendritic spines with immature morphology has been reported in brains of ASD patients (Hutsler and Zhang, 2010; Tang et al., 2014). Reducing p18 levels in WT mice resulted in similar changes in spine properties. It is therefore tempting to propose that UBE3A over-expression might induce ASD phenotypes, at least in part, by down-regulating p18 levels. It is also noteworthy that abnormal mTOR signaling has been implicated in a number of diseases. Therefore, the above results shed new light on a broad range of normal brain functions, and on several neurological/neuropsychiatric disorders, including AS.

REFERENCES

Attia N et al., 2018 (Drug Des Devel Ther. 2018 Nov. 16; 12:3937-3949. doi: 10.2147/DDDT.S178532. eCollection 2018.)

Bar-Peled L, Schweitzer L D, Zoncu R, and Sabatini D M. 2012. Ragulator is a GEF for the rag GTPases that signal amino acid levels to mTORC1. *Cell* 150, 1196-1208. DOI: https://doi.org/10.1016/j.cell.2012.07.032, PMID: 22980980

Baudry M, Kramar E, Xu X, Zadran H, Moreno S, Lynch G, Gall C, and Bi X. 2012. Ampakines promote spine actin polymerization, long-term potentiation, and learning in a mouse model of Angelman syndrome. *Neurobiol Dis* 47, 210-215. DOI: https://doi.org/10.1016/j.nbd.2012.04.002, PMID: 22525571

Bordeaux J, Welsh A, Agarwal S, Killiam E, Baquero M, Hanna J, Anagnostou V, and Rimm D. 2010. Antibody validation. *Biotechniques* 48, 197-209. DOI: https://doi.org/10.2144/000113382, PMID: 20359301

Cao C, Rioult-Pedotti M S, Migani P, Yu O, Tiwari R, Parang K, Spaller M R, Goebel D J, and Marshall J. 2013. Impairment of TrkB-PSD-95 signaling in Angelman syndrome. *PLoS Biol* 11, e1001478. DOI: https://doi.org/10.1371/journal.pbio.1001478, PMID: 23424281

Castellano B M, Thelen A M, Moldayski O, Feltes M, van der Welle R E, Mydock-McGrane L, Jiang X, van Eijkeren R J, Davis O B, Louie S M, et al. 2017. Lysosomal cholesterol activates mTORC1 via an SLC38A9-Niemann-Pick C1 signaling complex. *Science* 355, 1306-1311. DOI: https://doi.org/10.1126/science.aag1417, PMID: 28336668

Challis R C et al., 2019 (Nat Protoc. 2019 February; 14(2):379-414. doi: 10.1038/s41596-018-0097-3.)

Chowdhury S, Shepherd J D, Okuno H, Lyford G, Petralia R S, Plath N, Kuhl D, Huganir R L, and Worley P F. 2006. Arc/Arg3.1 interacts with the endocytic machinery to regulate AMPA receptor trafficking. *Neuron* 52, 445-459. DOI: https://doi.org/10.1016/j.neuron.2006.08.033, PMID: 17088211

Cook E H, Jr., Lindgren V, Leventhal B L, Courchesne R, Lincoln A, Shulman C, Lord C, and Courchesne E. 1997. Autism or atypical autism in maternally but not paternally derived proximal 15q duplication. *Am J Hum Genet* 60, 928-934. PMID: 9106540

Cong et al., Science. 2013 Feb. 15; 339(6121):819-23.

Costa-Mattioli M, and Monteggia L M. 2013. mTOR complexes in neurodevelopmental and neuropsychiatric disorders. *Nat Neurosci* 16, 1537-1543. DOI: https://doi.org/10.1038/nn.3546, PMID: 24165680 de Araujo M E G, Naschberger A, Furnrohr B G, Stasyk T, Dunzendorfer-Matt T, Lechner S, Welti S, Kremser L, Shivalingaiah G, Offterdinger M, et al. 2017. Crystal structure of the human lysosomal mTORC1 scaffold complex and its impact on signaling. *Science* 358, 377-381. DOI: https://doi.org/10.1126/science.aao1583, PMID: 28935770

Dindot S V, Antalffy B A, Bhattacharjee M B, and Beaudet A L. 2008. The Angelman syndrome ubiquitin ligase localizes to the synapse and nucleus, and maternal deficiency results in abnormal dendritic spine morphology. *Hum Mol Genet* 17, 111-118. DOI: https://doi.org/10.1093/hmg/ddm288, PMID: 17940072

Eskelinen E L. 2006. Roles of LAMP-1 and LAMP-2 in lysosome biogenesis and autophagy. *Mol Aspects Med* 27, 495-502. DOI: https://doi.org/10.1016/j.mam.2006.08.005, PMID: 16973206

Goo M S, Sancho L, Slepak N, Boassa D, Deerinck T J, Ellisman M H, Bloodgood B L, and Patrick G N. 2017. Activity-dependent trafficking of lysosomes in dendrites and dendritic spines. *J Cell Biol* 216, 2499-2513. DOI: https://doi.org/10.1083/jcb.201704068, PMID: 28630145

Greer P L, Hanayama R, Bloodgood B L, Mardinly A R, Lipton D M, Flavell S W, Kim T K, Griffith E C, Waldon Z, Maehr R, et al. 2010. The Angelman Syndrome protein Ube3A regulates synapse development by ubiquitinating arc. *Cell* 140, 704-716. DOI: https://doi.org/10.1016/j.cell.2010.01.026, PMID: 20211139

Ham D J, Lynch G S, and Koopman R. 2016. Amino acid sensing and activation of mechanistic target of rapamycin complex 1: implications for skeletal muscle. *Curr Opin Clin Nutr Metab Care* 19, 67-73. DOI: https://doi.org/10.1097/MCO.0000000000000240, PMID: 26560525

Hara K, Maruki Y, Long X, Yoshino K, Oshiro N, Hidayat S, Tokunaga C, Avruch J, and Yonezawa K. 2002. Raptor, a binding partner of target of rapamycin (TOR), mediates TOR action. *Cell* 110, 177-189. PMID: 12150926

He Y, Li D, Cook S L, Yoon M S, Kapoor A, Rao C V, Kenis P J, Chen J, and Wang F. 2013. Mammalian target of rapamycin and Rictor control neutrophil chemotaxis by regulating Rac/Cdc42 activity and the actin cytoskeleton. *Mol Biol Cell* 24, 3369-3380. DOI: https://doi.org/10.1091/mbc.E13-07-0405, PMID: 24006489

Hoshino D, Koshikawa N, and Seiki M. 2011. A p27 (kip1)-binding protein, p27RF-Rho, promotes cancer metastasis via activation of RhoA and RhoC. *J Biol Chem* 286, 3139-3148. DOI: https://doi.org/10.1074/jbc.M110.159715, PMID: 21087931

Huang W, Zhu P J, Zhang S, Zhou H, Stoica L, Galiano M, Krnjevic K, Roman G, and Costa-Mattioli M. 2013. mTORC2 controls actin polymerization required for consolidation of long-term memory. *Nat Neurosci* 16, 441-448. DOI: https://doi.org/10.1038/nn.3351, PMID: 23455608

Huber K M, Klann E, Costa-Mattioli M, and Zukin R S. 2015. Dysregulation of Mammalian Target of Rapamycin Signaling in Mouse Models of Autism. *J Neurosci* 35, 13836-13842. DOI: https://doi.org/10.1523/JNEUROSCI.2656-15.2015, PMID: 26468183

Hutsler J J, and Zhang H. 2010. Increased dendritic spine densities on cortical projection neurons in autism spectrum disorders. *Brain Res* 1309, 83-94. DOI: https://doi.org/10.1016/j.brainres.2009.09.120, PMID: 19896929

Jacinto E, Loewith R, Schmidt A, Lin S, Ruegg M A, Hall A, and Hall M N. 2004. Mammalian TOR complex 2 controls the actin cytoskeleton and is rapamycin insensitive. *Nat Cell Biol* 6, 1122-1128. DOI: https://doi.org/10.1038/ncb1183, PMID: 15467718

Jewell J L, Russell R C, and Guan K L. 2013. Amino acid signalling upstream of mTOR. *Nat Rev Mol Cell Biol* 14, 133-139. DOI: https://doi.org/10.1038/nrm3522, PMID: 23361334

Kim C, Rockenstein E, Spencer B, Kim H K, Adame A, Trejo M, Stafa K, Lee H J, Lee S J, and Masliah E. 2015. Antagonizing Neuronal Toll-like Receptor 2 Prevents Synucleinopathy by Activating Autophagy. *Cell Rep* 13, 771-782. DOI: https://doi.org/10.1016/j.celrep.2015.09.044, PMID: 26489461

Kim D H, Sarbassov D D, Ali S M, King J E, Latek R R, Erdjument-Bromage H, Tempst P, and Sabatini D M. 2002. mTOR interacts with raptor to form a nutrient-sensitive complex that signals to the cell growth machinery. *Cell* 110, 163-175. PMID: 12150925

Kotajima-Murakami et al. Molecular Brain (2019) 12:3.

Kramar E A, Lin B, Rex C S, Gall C M, and Lynch G. 2006. Integrin-driven actin polymerization consolidates long-term potentiation. *Proc Natl Acad Sci USA* 103, 5579-5584. DOI: https://doi.org/10.1073/pnas.0601354103, PMID: 16567651

Kumar S, Talis A L, and Howley P M. 1999. Identification of HHR23A as a substrate for E6-associated protein-mediated ubiquitination. *J Biol Chem* 274, 18785-18792. PMID: 10373495

Laplante M, and Sabatini D M. 2012. mTOR signaling in growth control and disease. *Cell* 149, 274-293. DOI: https://doi.org/10.1016/j.cell.2012.03.017, PMID: 22500797

Lin B, Kramar E A, Bi X, Brucher F A, Gall C M, and Lynch G. 2005. Theta stimulation polymerizes actin in dendritic spines of hippocampus. *J Neurosci* 25, 2062-2069. DOI: https://doi.org/10.1523/JNEUROSCI.4283-04.2005, PMID: 15728846

Lin C Y et al., 2019 (Brain Stimul. 2019 Apr. 27. pii: S1935-861X (19)30203-7. doi: 10.1016/j.brs.2019.04.011. [Epub ahead of print]).

Mühlebner A et al., J. Anat. (2019), doi: 10.1111/joa.12956.

Nada S, Hondo A, Kasai A, Koike M, Saito K, Uchiyama Y, and Okada M. 2009. The novel lipid raft adaptor p18 controls endosome dynamics by anchoring the MEK-ERK pathway to late endosomes. *EMBO J* 28, 477-489. DOI: https://doi.org/10.1038/emboj.2008.308, PMID: 19177150

Nada S, Mori S, Takahashi Y, and Okada M. 2014. p18/LAMTOR1: a late endosome/lysosome-specific anchor protein for the mTORC1/MAPK signaling pathway. *Methods Enzymol* 535, 249-263. DOI: https://doi.org/10.1016/13978-0-12-397925-4.00015-8, PMID: 24377928

Nojima H, Tokunaga C, Eguchi S, Oshiro N, Hidayat S, Yoshino K, Hara K, Tanaka N, Avruch J, and Yonezawa K. 2003. The mammalian target of rapamycin (mTOR) partner, raptor, binds the mTOR substrates p70 S6 kinase and 4E-BP1 through their TOR signaling (TOS) motif. *J Biol Chem* 278, 15461-15464. DOI: https://doi.org/10.1074/jbc.C200665200, PMID: 12604610

Pignatelli M, Piccinin S, Molinaro G, Di Menna L, Riozzi B, Cannella M, Motolese M, Vetere G, Catania M V, Battaglia G, et al. 2014. Changes in mGlu5 receptor-dependent synaptic plasticity and coupling to homer proteins in the hippocampus of Ube3A hemizygous mice modeling angelman syndrome. *J Neurosci* 34, 4558-4566. DOI: https://doi.org/10.1523/JNEUROSCI.1846-13.2014, PMID: 24672001

Rial Verde E M, Lee-Osbourne J, Worley P F, Malinow R, and Cline H T. 2006. Increased expression of the immediate-early gene arc/arg3.1 reduces AMPA receptor-mediated synaptic transmission. Neuron 52, 461-474. DOI: https://doi.org/10.1016/j.neuron.2006.09.031, PMID: 17088212

Risher M L, Fleming R L, Risher W C, Miller K M, Klein R C, Wills T, Acheson S K, Moore S D, Wilson W A, Eroglu C, et al. 2015. Adolescent intermittent alcohol exposure: persistence of structural and functional hippocampal abnormalities into adulthood. *Alcohol Clin Exp Res* 39, 989-997. DOI: https://doi.org/10.1111/acer.12725, PMID: 25916839

Sancak Y, Bar-Peled L, Zoncu R, Markhard A L, Nada S, and Sabatini D M. 2010. Ragulator-Rag complex targets mTORC1 to the lysosomal surface and is necessary for its activation by amino acids. *Cell* 141, 290-303. DOI: https://doi.org/10.1016/j.cell.2010.02.024, PMID: 20381137

Sancak Y, Peterson T R, Shaul Y D, Lindquist R A, Thoreen C C, Bar-Peled L, and Sabatini D M. 2008. The Rag GTPases bind raptor and mediate amino acid signaling to mTORC1. *Science* 320, 1496-1501. DOI: https://doi.org/10.1126/science.1157535, PMID: 18497260

Sare R M, Song A, Loutaev I, Cook A, Maita I, Lemons A, Sheeler C, and Smith C B. 2017. Negative Effects of Chronic Rapamycin Treatment on Behavior in a Mouse Model of Fragile X Syndrome. *Front Mol Neurosci* 10, 452. DOI: https://doi.org/10.3389/fnmol.2017.00452, PMID: 29375310

Sun J, Liu Y, Moreno S, Baudry M, and Bi X. 2015a. Imbalanced mechanistic target of rapamycin c1 and c2 activity in the cerebellum of angelman syndrome mice impairs motor function. *J Neurosci* 35, 4706-4718. DOI: https://doi.org/10.1523/JNEUROSCI.4276-14.2015, PMID: 25788687

Sun J, Liu Y, Tran J, O'Neal P, Baudry M, and Bi X. 2016. mTORC1-S6K1 inhibition or mTORC2 activation improves hippocampal synaptic plasticity and learning in Angelman syndrome mice. *Cell Mol Life Sci* 73, 4303-4314. DOI: https://doi.org/10.1007/500018-016-2269-z, PMID: 27173058

Sun J, Zhu G, Liu Y, Standley S, Ji A, Tunuguntla R, Wang Y, Claus C, Luo Y, Baudry M, et al. 2015b. UBE3A Regulates Synaptic Plasticity and Learning and Memory by Controlling SK2 Channel Endocytosis. *Cell Rep* 12, 449-461. DOI: https://doi.org/10.1016/j.celrep.2015.06.023, PMID: 26166566

Takei N, and Nawa H. 2014. mTOR signaling and its roles in normal and abnormal brain development. *Front Mol Neurosci* 7, 28. DOI: https://doi.org/10.3389/fnmol.2014.00028, PMID: 24795562

Talis A L, Huibregtse J M, and Howley P M. 1998. The role of E6AP in the regulation of p53 protein levels in human papillomavirus (HPV)-positive and HPV-negative cells. *J Biol Chem* 273, 6439-6445. PMID: 9497376

Tang G, Gudsnuk K, Kuo S H, Cotrina M L, Rosoklija G, Sosunov A, Sonders M S, Kanter E, Castagna C, Yamamoto A, et al. 2014. Loss of mTOR-dependent macroautophagy causes autistic-like synaptic pruning deficits. *Neuron* 83, 1131-1143. DOI: https://doi.org/10.1016/j.neuron.2014.07.040, PMID: 25155956

Thomanetz V, Angliker N, Cloetta D, Lustenberger R M, Schweighauser M, Oliveri F, Suzuki N, and Ruegg M A. 2013. Ablation of the mTORC2 component rictor in brain or Purkinje cells affects size and neuron morphology. *J Cell Biol* 201, 293-308. DOI: https://doi.org/10.1083/jcb.201205030, PMID: 23569215

Vogel-Ciernia A, Matheos D P, Barrett R M, Kramar E A, Azzawi S, Chen Y, Magnan C N, Zeller M, Sylvain A, Haettig J, et al. 2013. The neuron-specific chromatin regulatory subunit BAF53b is necessary for synaptic plasticity and memory. *Nat Neurosci* 16, 552-561. DOI: https://doi.org/10.1038/nn.3359, PMID: 23525042

Wagner S A, Beli P, Weinert B T, Nielsen M L, Cox J, Mann M, and Choudhary C. 2011. A proteome-wide, quantitative survey of in vivo ubiquitylation sites reveals widespread regulatory roles. *Mol Cell Proteomics* 10, M111013284. DOI: https://doi.org/10.1074/mcp.M111.013284, PMID: 21890473

Williams C A, Zori R T, Stone J W, Gray B A, Cantu E S, and Ostrer H. 1990. Maternal origin of 15q11-13 deletions in Angelman syndrome suggests a role for genomic imprinting. *Am J Med Genet* 35, 350-353. DOI: https://doi.org/10.1002/ajmg.1320350308, PMID: 2309781

Young J A, Sermwittayawong D, Kim H J, Nandu S, An N, Erdjument-Bromage H, Tempst P, Coscoy L, and Winoto A. 2011. Fas-associated death domain (FADD) and the E3 ubiquitin-protein ligase TRIM21 interact to negatively regulate virus-induced interferon production. *J Biol Chem* 286, 6521-6531. DOI: https://doi.org/10.1074/jbc.M110.172288, PMID: 21183682

Zada S, Noh H S, Baek S M, Ha J H, Hahm J R, and Kim D R. 2015. Depletion of p18/LAMTOR1 promotes cell survival via activation of p27 (kip1)-dependent autophagy under starvation. *Cell Biol Int* 39, 1242-1250. DOI: https://doi.org/10.1002/cbin.10497, PMID: 26032166

What is claimed:

1. An inhibitory RNA, comprising an RNA oligonucleotide that reduces the expression of p18, wherein the inhibitory RNA is shRNA, and wherein the shRNA comprises an RNA sequence with at least 80%, at least 85%, at least 90%, at least 95%, or 100% complementarity to SEQ ID NO: 1.

2. The inhibitory RNA of claim 1, comprising an RNA sequence with 100% complementarity to SEQ ID NO: 1.

3. A viral vector, encoding an inhibitory RNA according to claim 1.

4. A pharmaceutical composition, comprising the vector according to claim 3.

5. A pharmaceutical composition, comprising an inhibitory RNA according to claim 1.

6. A method for inhibiting p18 expression in a subject having a neurological disorder selected from the group consisting of Angelman Syndrome, Autism Spectrum Disorder, epilepsy, Tuberous Sclerosis Complex, Focal Cortical Dysplasia, and Fragile X syndrome, comprising administering the pharmaceutical composition of claim 4 to a subject in need thereof.

7. A method for inhibiting p18 expression in a subject having a neurological disorder selected from the group consisting of Angelman Syndrome, Autism Spectrum Disorder, epilepsy, Tuberous Sclerosis Complex, Focal Cortical Dysplasia, and Fragile X syndrome, comprising administering the pharmaceutical composition of claim 5 to a subject in need thereof.

* * * * *

SEQUENCE LISTING

```
<160> NUMBER OF SEQ ID NOS: 23

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
cgtatgccta tagtgcactt t                                                   21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gcgaaagaag agctggttgt a                                                   21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
cctgctacta atcacggaga a                                                   21

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
ccaactacca tagcctacct t                                                   21

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
gctggttgta cagtttggga t                                                   21

<210> SEQ ID NO 6
<211> LENGTH: 21
<212> TYPE: DNA
<213> ORGANISM: Artificial Sequence
```

```
<220> FEATURE:
<223> OTHER INFORMATION: Synthetic

<400> SEQUENCE: 6
gccctgcttt cctccatcct t                                              21

<210> SEQ ID NO 7
<211> LENGTH: 29
<212> TYPE: DNA
<213> ORGANISM: Artificial Sequence
<220> FEATURE:
<223> OTHER INFORMATION: Synthetic

<400> SEQUENCE: 7
agcccaacta ccatagccta ccttcagct                                      29

<210> SEQ ID NO 8
<211> LENGTH: 29
<212> TYPE: DNA
<213> ORGANISM: Artificial Sequence
<220> FEATURE:
<223> OTHER INFORMATION: Synthetic

<400> SEQUENCE: 8
tcccagggca tggaacagca tgagtacat                                      29

<210> SEQ ID NO 9
<211> LENGTH: 29
<212> TYPE: DNA
<213> ORGANISM: Artificial Sequence
<220> FEATURE:
<223> OTHER INFORMATION: Synthetic

<400> SEQUENCE: 9
tggaagaagc tgccaccgtt gccatctct                                      29

<210> SEQ ID NO 10
<211> LENGTH: 29
<212> TYPE: DNA
<213> ORGANISM: Artificial Sequence
<220> FEATURE:
<223> OTHER INFORMATION: Synthetic

<400> SEQUENCE: 10
cgcgtggatg cgaaagaaga gctggttgt                                      29

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
gcatggaaca gcatgagta                                                 19

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
gtacctaacc tgctactaa                                                 19
```

```
<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13
gcttgagtct gaattgagt                                                        19

<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
cctcgataaa gaaagtata                                                        19

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
gcgtggatgc gaaagaaga                                                        19

<210> SEQ ID NO 16
<211> LENGTH: 19
<212> TYPE: DNA
<213> ORGANISM: Artificial Sequence
<220> FEATURE:
<223> OTHER INFORMATION: Synthetic

<400> SEQUENCE: 16
tgcgtatgcc tatagtgca                                                        19

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
tccgctcgca ctgatgagca                                                       20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gatccgtgtg gacgcaaaag                                                       20

<210> SEQ ID NO 19
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 19

Lys Leu Leu Leu Asp Pro Ser Ser Pro Thr Lys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Tyr Gly Arg Lys Lys Arg Arg Gln Arg Arg
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Synthetic

<400> SEQUENCE: 21

Tyr Gly Arg Lys Lys Arg Arg Gln Arg Arg Lys Leu Leu Leu Asp
1               5                   10                  15

Pro Ser Ser Pro Pro Thr Lys
            20

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Tyr Gly Arg Lys Lys Arg Arg Gln Arg Arg Lys Glu Glu Leu Val
1               5                   10                  15

Val

<210> SEQ ID NO 23
<211> LENGTH: 161
<212> TYPE: PRT
<213> ORGANISM: Homo sapiens

<400> SEQUENCE: 23

Met Gly Cys Cys Tyr Ser Ser Glu Asn Glu Asp Ser Asp Gln Asp Arg
1               5                   10                  15

Glu Glu Arg Lys Leu Leu Leu Asp Pro Ser Ser Pro Pro Thr Lys Ala
            20                  25                  30

Leu Asn Gly Ala Glu Pro Asn Tyr His Ser Leu Pro Ser Ala Arg Thr
        35                  40                  45

Asp Glu Gln Ala Leu Leu Ser Ser Ile Leu Ala Lys Thr Ala Ser Asn
    50                  55                  60

Ile Ile Asp Val Ser Ala Ala Asp Ser Gln Gly Met Glu Gln His Glu
65                  70                  75                  80

Tyr Met Asp Arg Ala Arg Gln Tyr Ser Thr Arg Leu Ala Val Leu Ser
                85                  90                  95

Ser Ser Leu Thr His Trp Lys Lys Leu Pro Pro Leu Pro Ser Leu Thr
            100                 105                 110
```

```
-continued

Ser Gln Pro His Gln Val Leu Ala Ser Glu Pro Ile Pro Phe Ser Asp
        115                 120                 125

Leu Gln Gln Val Ser Arg Ile Ala Ala Tyr Ala Tyr Ser Ala Leu Ser
    130                 135                 140

Gln Ile Arg Val Asp Ala Lys Glu Glu Leu Val Val Gln Phe Gly Ile
145                 150                 155                 160

Pro
```